(12) United States Patent
Nelson et al.

(10) Patent No.: US 8,918,176 B2
(45) Date of Patent: Dec. 23, 2014

(54) ASSESSING COGNITIVE DISORDERS BASED ON NON-MOTOR EPILEPTIFORM BIOELECTRICAL BRAIN ACTIVITY

(71) Applicant: Medtronic, Inc., Minneapolis, MN (US)

(72) Inventors: Dwight E. Nelson, Shoreview, MN (US); Jonathon E. Giftakis, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 5 days.

(21) Appl. No.: 13/777,091

(22) Filed: Feb. 26, 2013

(65) Prior Publication Data

US 2014/0081347 A1 Mar. 20, 2014

Related U.S. Application Data

(60) Provisional application No. 61/637,035, filed on Apr. 23, 2012.

(51) Int. Cl.
*A61N 1/36* (2006.01)
*A61B 5/00* (2006.01)

(52) U.S. Cl.
CPC .......... *A61N 1/36139* (2013.01); *A61B 5/4852* (2013.01); *A61B 5/4088* (2013.01); *A61N 1/36082* (2013.01); *A61B 5/4094* (2013.01); *A61N 1/36064* (2013.01); *A61N 2001/36039* (2013.01)
USPC ............................................ 607/45; 600/544

(58) Field of Classification Search
CPC ................ A61N 1/36025; A61N 2001/36039; A61N 2001/3605; A61N 2001/3606; A61N 2001/36064; A61N 2001/36082; A61N 2001/36132; A61B 5/0476; A61B 5/4064; A61B 5/4088; A61B 5/4094; A61B 5/4842
USPC ...................................... 607/45; 600/544, 545
See application file for complete search history.

(56) References Cited

U.S. PATENT DOCUMENTS 6,597,954 B1 * 7/2003 Pless et al. ...................... 607/62
7,006,872 B2 2/2006 Gielen et al.
(Continued)

FOREIGN PATENT DOCUMENTS

EP 1145735 A2 10/2001
WO 2004-034882 A2 4/2004

OTHER PUBLICATIONS

Palop et al, Aberrant Excitatory Neuronal Activity and Compensatory Remodeling of Inhibitory Hippocampal Circuits in Mouse Models of Alzheimer's Disease, Neuron, vol. 55, Issue 5, Sep. 6, 2007, pp. 697-711, ISSN 0896-6273.*

(Continued)

*Primary Examiner* — Carl H Layno
*Assistant Examiner* — Eugene Wu
(74) *Attorney, Agent, or Firm* — Beth L. McMahon

(57) ABSTRACT

Various embodiments concern assessing a degenerative cognitive disorder of a patient based on a plurality of episodes of non-motor epileptiform bioelectrical activity. The non-motor epileptiform bioelectrical activity can be detected from one or more bioelectrical brain signals. A worsening cognitive disorder may be indicated by an increase in one or more of intensity, duration, and frequency of occurrence of the episodes of non-motor epileptiform bioelectrical activity. A therapy can be delivered to reduce one or more of intensity, duration, and frequency of occurrence of the episodes of non-motor epileptiform bioelectrical activity. The delivery of the therapy can be controlled based on the plurality of episodes of non-motor epileptiform bioelectrical activity.

39 Claims, 11 Drawing Sheets

(56) References Cited

U.S. PATENT DOCUMENTS

| | | | |
|---|---|---|---|
| 2005/0197678 | A1 | 9/2005 | Boveja et al. |
| 2006/0212090 | A1 | 9/2006 | Lozano et al. |
| 2006/0265022 | A1 | 11/2006 | John et al. |
| 2009/0082691 | A1 | 3/2009 | Denison et al. |
| 2009/0099623 | A1* | 4/2009 | Bentwich .................. 607/45 |
| 2009/0137921 | A1* | 5/2009 | Kramer et al. ............. 600/544 |
| 2010/0114237 | A1 | 5/2010 | Giftakis et al. |
| 2010/0121215 | A1 | 5/2010 | Giftakis et al. |
| 2010/0280334 | A1 | 11/2010 | Carlson et al. |
| 2010/0280335 | A1 | 11/2010 | Carlson et al. |
| 2012/0116475 | A1 | 5/2012 | Nelson et al. |

OTHER PUBLICATIONS

A. Soren Leonard, James O. McNamara, Does Epileptiform Activity Contribute to Cognitive Impairment in Alzheimer's Disease?, Neuron, vol. 55, Issue 5, Sep. 6, 2007, pp. 677-678, ISSN 0896-6273.*

Vossel, "Seizures and epileptiform activity in the early stages of Alzheimer disease.", JAMA Neurol. Sep. 1, 2013;70(9):1158-66. doi: 10.1001/jamaneurol.2013.136.*

Albert P. Aldenkamp, Johan Arends, Effects of epileptiform EEG discharges on cognitive function: is the concept of "transient cognitive impairment" still valid?, Epilepsy & Behavior, vol. 5, Supplement 1, Feb. 2004, pp. 25-34, ISSN 1525-5050.*

Palop et al. "Epilepsy and Cognitive Impairments in Alzheimer Disease." Arch Neurol. 2009;66(4):435-440.*

Rabinowicz et al. "Transient epileptic amnesia in dementia: a treatable unrecognized cause of episodic amnestic wandering." Alzheimer Dis Assoc Disord. Oct.-Dec. 2000;14(4):231-3. Abstract via PubMed.*

Pritchard et al. "Epileptic amnesic attacks: benefit from antiepileptic drugs." Neurology. Aug. 1985;35(8):1188-9. Abstract via PubMed.*

Sinforiani et al. "Memory disturbances and temporal lobe epilepsy simulating Alzheimer's disease: a case report." Funct Neurol. Jan.-Mar. 20003;18(1):39-41. Abstract via PubMed.*

Marcelo Heitor Ferreira Mendes, Transient epileptic amnesia: an under-diagnosed phenomenon? Three more cases, Seizure, vol. 11, Issue 4, Jun. 2002, pp. 238-242.*

U.S. Appl. No. 61/527,387, filed Aug. 25, 2011.

U.S. Appl. No. 61/436,059, filed Jan. 25, 2011.

Suthana, et al., "Memory Enhancement and Deep-Brain Stimulation of the Entorhinal Area," N Engl J Med 366:6, Feb. 9, 2012, pp. 502-510.

Laxton, et al., "A Phase 1 Trial of Deep Brain Stimulation of Memory Circuits in Alzheimer's Disease," Wiley Interscience, www.interscience.wiley.com, May 19, 2010, pp. 1-14.

Alvarez, et al., "Damage Limited to the Hippocampal Region Produces Long-Lasting Memory Impairment in Monkeys," Journal of Neuroscience, May 1995, 15(5), pp. 3796-3807.

Gleichmann, et al., "Alzheimer's Disease and Neuronal Network Activity", Neuromol Med, Nov. 3, 2009, 4 pgs.

Palop, et al., "Synaptic Depression and Aberrant Excitatory Network Activity in Alzheimer's Disease: Two Faces of the Same Coin?" Neuromol Med, Oct. 17, 2009, 8 pgs.

Palop, et al., "Epilepsy and Cognitive Impairments in Alzheimer Disease," Arch Neurol, Apr. 2009, 66(4): 435, 11 pgs.

"Anti-Seizure Drug Slows Progress of Pre-Alzheimer's Condition, Study Finds," http://nursing.advanceweb.com/News/National-News/Anti-Seizure-Drug-Slows-Progress-of-Pre-Alzheimers-Conditon-Study-Finds.aspx, Jul. 26, 2011.

Fisch, "Fisch and Spehlmann's EEG Primer—Basic Principles of Digital and Analog EEG," Elsevier Science BV, 1999, pp. 145-146, 237-240, 367-368), 8 pgs.

International Search Report and Written Opinion, PCTUS2013/027978, Jun. 4, 2013, 10 pgs.

* cited by examiner

1100

ASSESSING COGNITIVE DISORDERS BASED ON NON-MOTOR EPILEPTIFORM BIOELECTRICAL BRAIN ACTIVITY

TECHNICAL FIELD

The disclosure relates to medical devices and, more particularly, to medical devices for tracking a cognitive disorder and/or delivering therapeutic brain stimulation.

BACKGROUND

Implantable medical devices, such as electrical stimulation devices, may be used in different therapeutic applications, such as for deep brain stimulation (DBS), spinal cord stimulation (SCS), pelvic stimulation, gastric stimulation, peripheral nerve stimulation, or functional electrical stimulation of a target tissue site within a patient. An electrical stimulation device may be used to treat a variety of symptoms or conditions of a patient, such as chronic pain, tremor, Alzheimer's disease, Parkinson's disease, other types of movement disorders, seizure disorders (e.g., epilepsy), urinary or fecal incontinence, sexual dysfunction, obesity, mood disorders, gastroparesis, or diabetes. In some therapy systems, an implantable electrical stimulator delivers electrical therapy to a target tissue site within a patient with the aid of one or more electrodes, which may be deployed by medical leads.

SUMMARY

Various embodiments concern treating a cognitive disorder of a patient by sensing one or more bioelectrical brain signals of the patient using one or more electrodes, detecting non-motor epileptiform bioelectrical activity from the one or more bioelectrical brain signals, assessing a degenerative cognitive disorder of the patient based on the non-motor epileptiform bioelectrical activity, and controlling delivery of an electrical stimulation therapy to the brain of the patient to treat the cognitive disorder, the delivery of the electrical stimulation therapy controlled based on the assessment of the cognitive disorder. In some cases, assessing the cognitive disorder may comprise determining whether episodes of the non-motor epileptiform bioelectrical activity are changing in one or more of intensity, duration, and frequency of occurrence.

In some cases, the electrical stimulation therapy decreases one or more of the intensity, duration, and frequency of occurrence of episodes of the non-motor epileptiform bioelectrical activity associated with the cognitive disorder. Controlling the delivery of the electrical stimulation therapy based on the assessment may comprise increasing intensity of the electrical stimulation therapy if the cognitive disorder is assessed to be worsening. Controlling the delivery of the electrical stimulation therapy based on the assessment may comprise increasing the intensity of the electrical stimulation therapy based on episodes of the non-motor epileptiform bioelectrical activity increasing in one or more of intensity, duration, and frequency of occurrence. Also, controlling the delivery of the electrical stimulation therapy based on the assessment may comprise decreasing the intensity of the electrical stimulation therapy based on episodes of the non-motor epileptiform bioelectrical activity decreasing in one or more of intensity, duration, and frequency of occurrence. Controlling the delivery of the electrical stimulation therapy may comprise initiating the delivery of a series of pulses in response to the detection of each episode of non-motor epileptiform bioelectrical activity.

Some embodiments may further comprise tracking a second indicator of the cognitive disorder, wherein the second indicator is not based on a sensed bioelectrical signal and the assessment of the cognitive disorder is further based on the second indicator. The assessment of the cognitive disorder can be based on corroboration between the second indicator and the non-motor epileptiform bioelectrical activity. The second indicator may be measured based on the patient's performance on a cognitive test testing cognitive ability. The second indicator may comprise an input by a user to an external programmer.

Each episode of non-motor epileptiform bioelectrical activity may be detected as one or more of an irregular spike, a sharp wave, and a spike-and-wave complex that stands out as a transient in the sensed bioelectrical brain signal, in some embodiments. Some embodiments may comprise, for at least one episode of non-motor epileptiform bioelectrical activity, confirming that the episode is not temporally associated with a physical event indicative of a motor seizure. Some embodiments may further comprise receiving a signal from a sensor, the sensor monitoring for a physical non-bioelectrical manifestation of the motor seizure, wherein the signal is used to confirm that the episode is not temporally associated with the physical event.

Any and/or all of the above steps may be carried out by sensing circuitry configured to sense one or more bioelectrical brain signals of the patient using at least one electrode of a plurality of electrodes of one or more leads, a stimulation generator configured to deliver an electrical stimulation therapy to the brain to treat the degenerative cognitive disorder of the patient, the electrical stimulation therapy delivered through one or more electrodes of the plurality of electrodes, and control circuitry configured to perform each of the described functions. The control circuitry may be contained with an implantable medical device or distributed between the implantable medical device and an external programmer.

Various embodiments concern a system for treating a cognitive disorder of a patient comprising means for sensing one or more bioelectrical brain signals of the patient, means for detecting non-motor epileptiform bioelectrical activity from the one or more bioelectrical brain signals, means for assessing a degenerative cognitive disorder of the patient based on the non-motor epileptiform bioelectrical activity, and means for delivering an electrical stimulation therapy to the brain of the patient to treat the cognitive disorder, the delivery of the electrical stimulation therapy controlled based on the assessment of the cognitive disorder.

Various embodiments concern a physically embodied computer-readable medium comprising instructions executable by a processor to cause circuitry to sense one or more bioelectrical brain signals from the brain of a patient, detect non-motor epileptiform bioelectrical activity from the one or more bioelectrical brain signals, assess a degenerative cognitive disorder of the patient based on the non-motor epileptiform bioelectrical activity, and control delivery of an electrical stimulation therapy to the brain of the patient to treat the cognitive disorder, the delivery of the electrical stimulation therapy controlled based on the assessment of the cognitive disorder.

Various embodiments concern treating a cognitive disorder of a patient by sensing one or more bioelectrical brain signals of the patient using one or more electrodes, detecting excessive hippocampal bioelectrical activity from the one or more bioelectrical brain signals, assessing a degenerative cognitive disorder of the patient based on the excessive hippocampal bioelectrical activity, and controlling delivery of an electrical stimulation therapy to the brain of the patient to treat the cognitive disorder, the delivery of the electrical stimulation therapy controlled based on the assessment of the cognitive disorder, wherein sensing, detecting, assessing, and delivering are each performed at least in part by control circuitry.

DETAILED DESCRIPTION

Figure 1:
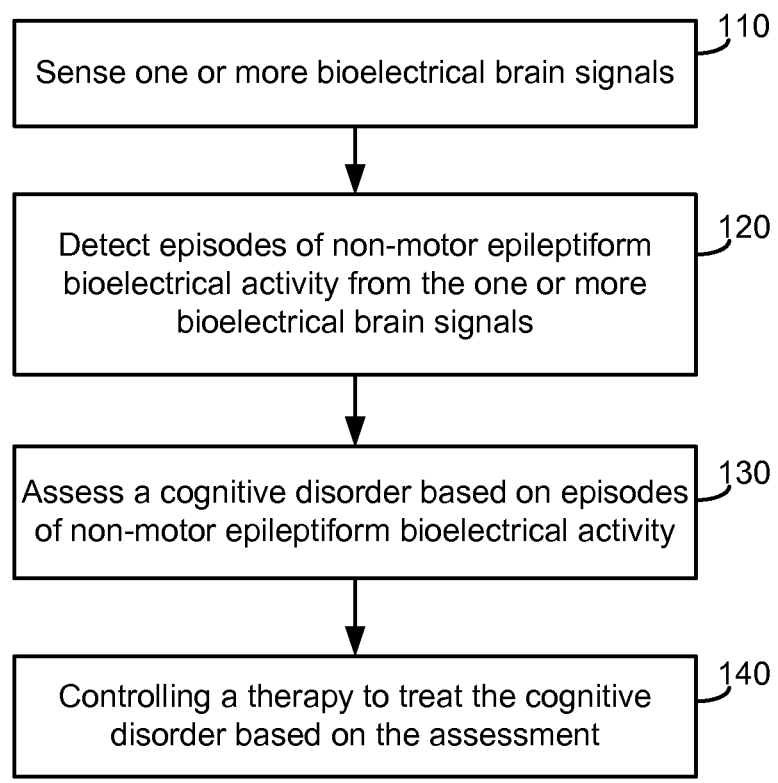
FIG. 1 is a flowchart for assessing a cognitive disorder and controlling a therapy based on non-motor epileptiform bioelectrical activity.

Alzheimer's disease is a type of dementia marked by worsening memory and cognitive impairment. Alzheimer's disease may manifest in short term memory impairment, inattentiveness, apathy, and mild cognitive and motor difficulties in early stages. Midterm stages of Alzheimer's disease can include impairment of speech and complex motor skills, delusion, long term memory loss, and moderate cognitive impairment. Advanced stages can include the total loss of language, discernable cognition, and the ability to care for oneself for even the most simple of matters. The complications of Alzheimer's disease are often contributing factors in death. There is no consensus on the cause of Alzheimer's disease and there is no recognized cure.

While each patient's Alzheimer's disease onset and progression of symptoms are different, the above symptoms, as well as other symptoms, can be used to track progression of the disease. Tracking the progression of Alzheimer's disease through observation, both by the patient and other people (e.g., family and/or health professionals) of these impairment-type symptoms can be difficult and inconsistent. Such tracking is subjective, hard to quantify, and in some cases is dependent on the self-reflection and self-reporting abilities of the patient. Tracking the progression of Alzheimer's disease through such observation can further be complicated by patients who have frequent and inexplicable fluctuations between "good days" of relatively less impairment and "bad days" of relatively greater impairment. Moreover, to the extent that such observation of symptoms of Alzheimer's disease only tracks an outward manifestation of Alzheimer's disease, such techniques often miss pre- and early Alzheimer's disease phases. These complications can also be experienced with other degenerative cognitive disorders. The present disclosure provides, among other things, a biomarker that can be used to assess cognitive disorders. Such cognitive disorders may include Alzheimer's disease, mild cognitive impairment, and others.

The brain is comprised of various networks interconnected by neurons. Some of these networks may activate or deactivate to carry out a function and/or induce a particular state of mind. The neurons of the networks may depolarize ("fire") in coordination (e.g., at a specific oscillatory frequency) and generate bioelectrical activity. One network may interact with other brain networks in coordination or antagonism to support proper brain function. While cognitive disorders may manifest as mild to severe memory and/or concentration deficiencies, abnormal bioelectrical brain activity can underlie these conditions. It is believed that epileptiform bioelectrical activity is associated with various cognitive disorders. For example, episodes of non-motor epileptiform bioelectrical activity may precede or track a decline in cognitive ability. Of particular interest herein are episodes of non-motor epileptiform bioelectrical activity.

Epileptic bioelectrical brain patterns are associated with seizures in epilepsy patients. However, patients without seizures can also have bioelectrical brain patterns similar to the epileptic bioelectrical brain patterns of epilepsy patients, but without clinical manifestations of seizures. These bioelectrical brain patterns are referred to herein as non-motor epileptiform bioelectrical activity episodes because they are bioelectrically similar to epileptic bioelectrical brain patterns but are unassociated with movement disorders (i.e. the patient does not experience symptoms of seizure in association with the non-motor epileptiform bioelectrical activity episodes). Non-motor epileptiform bioelectrical activity episodes may precede clinical manifestations of cognitive disorders such as slowed thinking, lack of concentration and/or memory deficits. For example, a patient may have non-motor epileptiform bioelectrical activity episodes for months preceding development of a cognitive disorder. Moreover, a patient may have an increasing number of non-motor epileptiform bioelectrical activity episodes while the cognitive disorder progresses, such as with worsening of slowed thinking, lack of concentration, and/or memory deficits. In some cases, many episodes of non-motor epileptiform bioelectrical activity over time may result in damage to the brain (e.g., including but not necessarily limited to the hippocampus), whether by the episodes directly damaging the brain, the damage occurring as a result of the brain network's response to the episodes, or some other mechanism. The additive damage can accelerate the decline of brain function as part of a degenerative cognitive disorder.

Chronic monitoring and tracking of non-motor epileptiform bioelectrical activity episodes can track the progression of a cognitive disorder and provide an objective measure of the state of the cognitive disorder. The non-motor epileptiform bioelectrical activity episodes can further be used to control an electrical stimulation therapy delivered to the brain to address the cognitive disorder.

In various embodiments, therapy delivery can be controlled based on the tracking of the cognitive disorder. A cognitive disorder can be tracked by identifying episodes of non-motor epileptiform bioelectrical activity from bioelectrical brain signals. Quantitative measures of the episodes can be generated based on frequency, length, intensity, and relative amount of time where the episodes are present, among other measures. Generally, more frequent, more intense, and longer episodes of non-motor epileptiform bioelectrical activity are indicative of a worsening brain condition, such as Alzheimer's disease or pre-Alzheimer's disease or other degenerative cognitive disorder, while less frequent, less intense, and shorter episodes of co-activation are indicative of an improving or relatively better brain condition. Therapy treating the brain condition underlying the cognitive disorder, or treating the symptoms, can be titrated based on the identification of the episodes, such as adjusting therapy intensity based on whether the episodes indicate an improving or worsening cognitive disorder condition. The efficacy of therapy in addressing the condition or the symptoms can be evaluated based on the episodes. Various embodiments are discussed in connection with the Figures presented herein.

FIG. 1 illustrates a flowchart of a method 100 for assessing a cognitive disorder and further controlling a therapy based on episodes of non-motor epileptiform bioelectrical activity. The method 100 includes sensing 110 one or more bioelectrical brain signals. Sensing 110 can include receiving one or more bioelectrical signals into sensing circuitry through an electrode within or proximate the brain. The sensing circuitry may condition the signals (e.g., through the use of filters) and/or measure the amplitude or other parameter(s) of the signals. The bioelectrical brain signals may be any electrical signals, including but not limited to local field potentials (LFP), electroencephalography (EEG) signals, or electrocorticography (ECoG) signals. Sensing 110 may be performed by an implantable medical device in some embodiments. Sensing 110 may be performed at least in part by an external device in some embodiments.

The method 100 further includes detecting 120 non-motor epileptiform bioelectrical activity from the sensed 110 bioelectrical brain signals. Detection 120 of non-motor epileptiform bioelectrical activity may be done in any manner referenced herein, such as by detecting an irregular spike or sharp wave that stands out as a transient in the sensed 110 bioelectrical brain signal. Detection of non-motor epileptiform bioelectrical activity from bioelectrical brain signals is further discussed herein.

The method 100 further includes assessing 130 a cognitive disorder based on the detected 120 non-motor epileptiform bioelectrical activity. Assessing 130 the cognitive disorder can include determining the number of non-motor epileptiform bioelectrical activity episodes over a time period, determining the rate of occurrence of non-motor epileptiform bioelectrical activity episodes, determining the intensity of the non-motor epileptiform bioelectrical activity, and/or determining the trend of the non-motor epileptiform bioelectrical activity, among other statistical techniques. The statistical techniques can be used to determine the relative level of non-motor epileptiform bioelectrical activity that is occurring. In some cases, the statistical metrics can be compared to a scale (e.g., a ten point scale covering severity levels of the cognitive disorder), a threshold (e.g., representing the presence or absence of a particular cognitive disorder), population data (e.g., representing the prevalence of non-motor epileptiform bioelectrical in healthy individuals or individuals having a particular cognitive disorder), past data for the same patient (e.g., previously collected), and/or other data to characterize the patient's cognitive disorder. The assessment 130 can include determining whether a cognitive disorder is present or absent, such as by diagnosing a patient as having a particular cognitive disorder based on the prevalence of non-motor epileptiform bioelectrical activity episodes (e.g., whether the number, rate of occurrence, or another measure of the prevalence of episodes crosses a threshold). The assessment may be used to track the cognitive disorder and provide an output in some embodiments. Such an output may comprise a report printed out and/or displayed on a screen of a computing device such as a programmer.

Some embodiments of the method 100 may further include controlling 140 delivery of a therapy to the brain to treat the cognitive disorder. The delivery of the therapy may be controlled 140 based on the assessment 130 of the cognitive disorder, as further discussed herein. The therapy may be a drug therapy, such as by prescribing, administering, delivering, and/or infusing (e.g., with an implantable drug pump) a drug to a patient. The therapy may additionally or alternatively include an electrical stimulation therapy, such as delivering a series of pulses to the brain of the patient in the manner of DBS. Controlling 140 can include but is not limited to initiating delivery of the therapy, increasing the intensity of the therapy, decreasing the intensity of the therapy, and/or stopping the delivery of the therapy.

In some cases, an assessment 130 of a cognitive disorder may identify signs of pre-Alzheimer's disease, pre-cognitive impairment, or some other state where clinical symptoms are not yet identifiable or established, but the bioelectrical activity of the brain evidences non-motor epileptiform bioelectrical activity as a biomarker for a preliminary stage of the degenerative cognitive condition. A threshold or other standard of non-motor epileptiform bioelectrical activity can be established representing pre-Alzheimer's disease, pre-cognitive impairment, or some other preliminary stage of a degenerative cognitive disorder. If the assessment 130 determines that the detected 120 non-motor epileptiform bioelectrical activity crosses the threshold, then an output can be made by a medical device. Such an output can include generating a report and/or delivering 140 therapy.

Non-motor epileptiform bioelectrical activity can be characterized as irregular spikes, sharp waves, and/or spike-and-wave complexes that standout as abnormal transients of a bioelectrical brain signal unassociated with any physical or outward manifestation. In some cases, non-motor epileptiform bioelectrical activity may bioelectrically resemble an epileptic seizure but be unassociated with any physical or outward manifestation. In some cases, a spike has a duration of 20-70 milliseconds while a sharp wave is longer with a duration of 70-200 milliseconds. In some cases, the irregular spikes, sharp waves, and/or spikes-and-waves may occur at a low frequency (e.g., about 2-3 Hz). Control circuitry running one or more algorithms may automatically detect non-motor epileptiform bioelectrical activity based on these characteristics. The epileptiform bioelectrical activity can be sensed, in various embodiments, from the temporal structures.

In some cases, a baseline of bioelectrical activity can be established for a patient to facilitate detection of non-motor epileptiform bioelectrical activity or other events. A bioelectrical brain signal can be sensed during a period of time during which no abnormal bioelectrical events occur, including no non-motor epileptiform bioelectrical activity, seizures, or electrical stimulation. The sensed signal can be visually observed on a screen or as a printout to confirm that no abnormal events are reflected in the signal. From this sensed signal, a baseline level of bioelectrical activity can be established, the baseline reflecting the amount of brain activity normally present in the absence of abnormal bioelectrical events. The average, mean, standard deviation, variability, and/or other statistical function can be calculated from the amplitude of the bioelectrical brain signal over the time period to represent the baseline. In some cases, the root mean square (RMS), spectral energy, or other parameter of signal energy can be calculated to represent the baseline. The baseline level of bioelectrical activity can then serve as a reference for comparing a sensed bioelectrical signal and detecting non-motor epileptiform bioelectrical activity or other abnormal events In various embodiments, non-motor epileptiform bioelectrical activity can be detected by control circuitry using criteria based on any of the above mentioned time domain characteristics of non-motor epileptiform bioelectrical activity. For example, a peak detector could identify a transient spike and/or sharp wave that is some predetermined amount above the baseline level (or deviating from baseline by a predetermined amount). For example, a detector could identify an amplitude peak of the bioelectrical brain signal that is 50% (or some other threshold amount) greater than baseline bioelectrical activity level. In some embodiments, a duration constraint may be used to identify a peak, such as a requirement that the duration of the spike or sharp wave fits within a widow of time (e.g., 20-70 milliseconds or 70-200 milliseconds depending on the type of biomarker). Other metrics that could be used to detect non-motor epileptiform bioelectrical activity includes peak-to-peak instantaneous amplitude, the peak-to-peak variability, or the peak first derivative of the bioelectrical signal, among others. Other parameters besides amplitude are also contemplated for measuring a change from a baseline level of bioelectrical activity to characterize non-motor epileptiform bioelectrical activity. In various embodiments, the change in the signal relative to a baseline must be greater than a threshold amount for control circuitry to confirm a particular event or brain state, such as a non-motor epileptiform bioelectrical activity event.

In some embodiments, control circuitry may perform temporal correlation by sampling the waveform generated by a sensed bioelectrical brain signal with a sliding window and comparing the waveform with a template waveform stored in memory that is associated with non-motor epileptiform bioelectrical activity (e.g., where the template was previously identified by a clinician as resembling non-motor epileptiform bioelectrical activity). For example, a correlation analysis may be performed by moving a window along a digitized plot of the amplitude waveform of a sensed bioelectrical brain signal at regular intervals, such as between about one millisecond to about ten millisecond intervals (or other time interval), to define a sample of the bioelectrical brain signal. The sample window can be slid along the plot until a correlation is detected between the waveform of the template and the waveform of the sample of the brain signal defined by the window. By moving the window at regular time intervals, multiple sample periods are defined. The correlation may be detected by, for example, matching multiple points between the template waveform indicative of non-motor epileptiform bioelectrical activity and the waveform of the plot of the sensed bioelectrical brain signal, or by applying any suitable mathematical correlation algorithm between the sample in the sampling window and a corresponding set of samples stored in the template waveform.

In various embodiments, control circuitry may identify non-motor epileptiform bioelectrical activity based on a frequency domain characteristic of a bioelectrical brain signal. Examples of frequency domain characteristics include, but are not limited to, a power level in one or more frequency bands of a bioelectrical signal sensed over a predetermined period of time or a ratio of power levels in at least two frequency bands of the bioelectrical brain signal. The frequency domain characteristic can be determined based on, for example, a spectral analysis of a bioelectrical brain signal. The spectral analysis may indicate the distribution over frequency of the power contained in a signal based on a finite set of data. In various embodiments, the frequency domain characteristic may comprise a relative power level in a particular frequency band or a plurality of frequency bands that have been identified as being associated with non-motor epileptiform bioelectrical activity for that particular patient (e.g., by first having a clinician supervised training phase with the patient). While "power levels" or "energy levels" within a selected frequency band of a sensed bioelectrical brain signal are generally referred to herein, the power or energy level may be a relative power or energy level. A relative power or energy level may include a ratio of a power level in a selected frequency band of a sensed brain signal to the overall power of the sensed brain signal. The power or energy level in the selected frequency band may be determined using any suitable technique.

Figure 2:
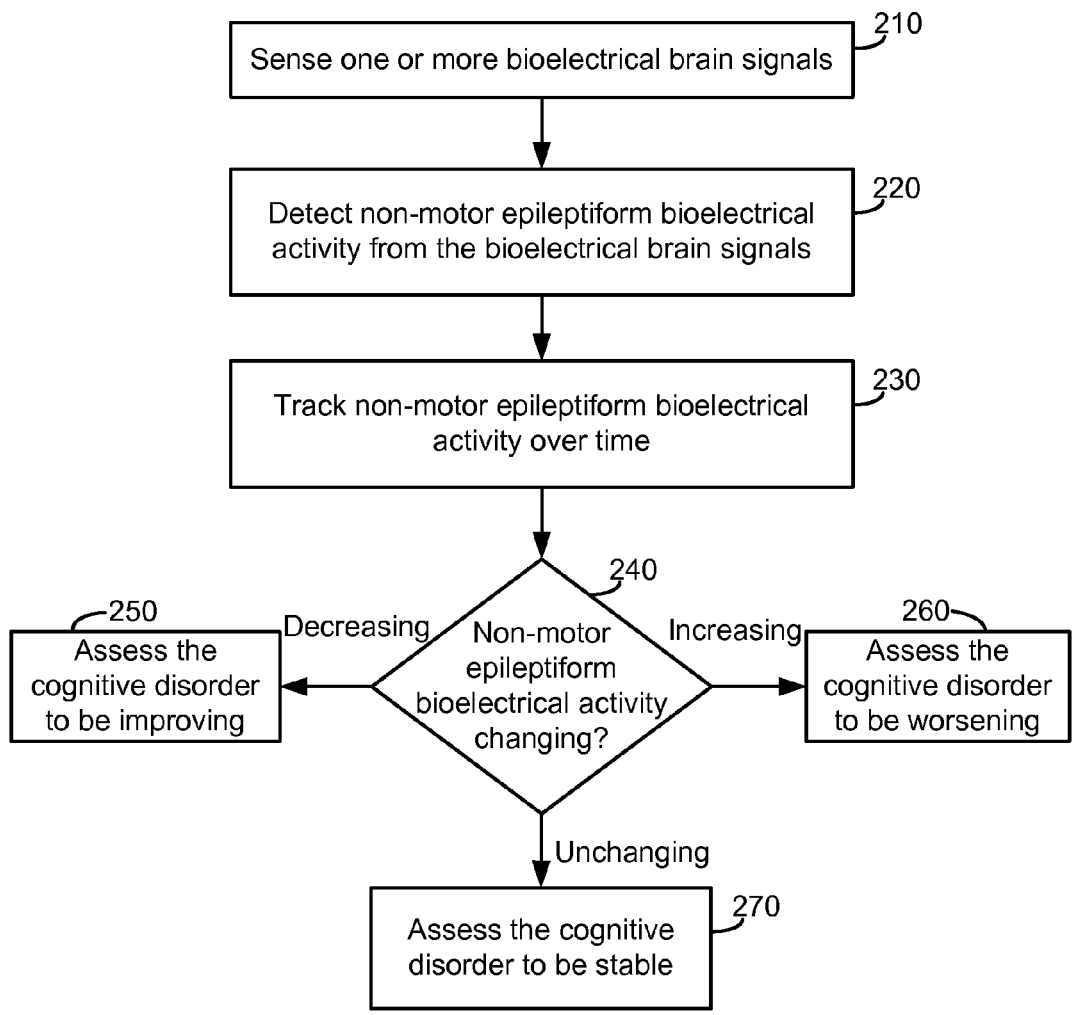
FIG. 2 is a flowchart for assessing a cognitive disorder based on non-motor epileptiform bioelectrical activity.

FIG. 2 shows a flowchart of a method 200 for assessing a cognitive disorder. The assessment of the cognitive disorder in the method 200 of FIG. 2 can correspond to the assessment 130 of FIG. 1. The method 200 includes sensing 210 bioelectrical brain signals, which for example can be done in any manner described in connection with FIG. 1 or elsewhere herein. The method 200 further includes detecting 220 non-motor epileptiform bioelectrical activity from the bioelectrical brain signals. Detecting 220 of the non-motor epileptiform bioelectrical activity can be done in any manner, such as in the manner described in connection with FIG. 1 or elsewhere herein.

The method 200 further includes tracking 230 non-motor epileptiform bioelectrical activity over time based on the detections 220 of non-motor epileptiform bioelectrical activity. Tracking 230 may include saving the signals, or portions of the signals, indicative of non-motor epileptiform bioelectrical activity in memory. A record may be saved in memory for each identification of a non-motor epileptiform bioelectrical episode. The record may include information characterizing the episode, such as the time of occurrence of the episode, the duration of the episode, contextual information (e.g., whether the patient was asleep or awake), a measure of the intensity of the episode (e.g., the maximum or average amplitude of the episode or the spectral energy of the signal indicating the episode), and/or how the episode was identified (e.g., what algorithm or template was used for detection), among other things. Higher bioelectrical amplitude and/or higher spectral energy of a bioelectrical signal during an episode can indicate a more intense non-motor epileptiform bioelectrical activity episode while lower bioelectrical amplitude and/or lower spectral energy of the bioelectrical signal during the episode can indicate a less intense non-motor epileptiform bioelectrical activity episode.

Tracking 230 may include summarizing information for multiple episodes or otherwise aggregating episode information. In some embodiments, the rate of episode occurrence (e.g., number of episodes per minute or hour) can be calculated from multiple episodes over a period of time. In some embodiments, the relative amount of time episodes are occurring (e.g., number of minutes per hour or day during which episodes occur) can be calculated from multiple episodes over a period of time. In some embodiments, the average episode duration, the average episode intensity (e.g., maximum or average signal amplitude), or some other aggregate measure can be calculated from multiple episodes sensed over a period of time. Such metrics may be stored in memory for later reference and comparison.

The tracking 230 of the non-motor epileptiform bioelectrical activity can be used to determine whether the non-motor epileptiform bioelectrical activity is changing 240. A previously determined metric characterizing the non-motor epileptiform bioelectrical activity from an earlier time period can be compared to a more recently determined metric characterizing the non-motor epileptiform bioelectrical activity from a later time period (e.g., such as a current time period). For example, a previously calculated rate of episode occurrence from a time period from a day ago, a month ago, or a year ago (or some other previous time period) may be compared to a current rate of episode occurrence from a time period corresponding to the current day, month, or year.

A comparison between metrics characterizing the non-motor epileptiform bioelectrical activity over different time periods may indicate that the non-motor epileptiform bioelectrical activity is decreasing, increasing, or is unchanged between the time periods. For example, if the rate of episode occurrence decreased between the different time periods, then the cognitive disorder may be assessed 250 to be improving based on the decreased frequency of episode occurrence. Likewise, a decreasing total number of episodes for different time periods, a decreasing average intensity for episodes of different time periods, and a decreasing relative amount of time episodes occurring for different time periods can each be the basis for assessing 250 a cognitive disorder condition to be improving. Conversely, if the rate of episode occurrence increased between the different time periods, then the cognitive disorder may be assessed 260 to be worsening based on the increased frequency of episode occurrence. Likewise, an increasing total number of episodes for different time periods, an increasing intensity for episodes of different time periods, and an increasing relative amount of time episodes are occurring for different time periods (or any other metric) can each be the basis for assessing 260 a cognitive disorder condition to be worsening or changing in some other way.

If the metric characterizing the non-motor epileptiform bioelectrical activity is unchanged over different time periods, then the cognitive disorder can be assessed 270 to be stable. In some embodiments, a threshold amount of a change in a metric characterizing the non-motor epileptiform bioelectrical activity between different time periods is needed to consider the cognitive disorder to be improving or worsening. As such, a cognitive disorder can be assessed 270 to be unchanged despite small changes in a metric over time, while a larger increase in the metric may cross the threshold to have the cognitive disorder to be assessed 260 as worsening or a larger decrease in a metric may cross the threshold to have the cognitive disorder to be assessed 250 as improving.

In some embodiments, a comparison of non-motor epileptiform bioelectrical activity to an absolute standard is made to assess a degenerative cognitive disorder of a patient. The absolute standard can be determined by a clinician or based on population data for example, where the absolute standard may represent different stages of a degenerative cognitive disorder. Comparing the non-motor epileptiform bioelectrical activity to the absolute standard may determine which state of the cognitive disorder the patient is in, such as a pre-disease state or an advanced state of the disease. Increasing indicators of non-motor epileptiform bioelectrical activity may mark a transition from a pre-disease state to a clinical disease state and from a clinical disease state to an advanced disease state.

Various actions can be taken depending on whether a cognitive disorder is assessed to be improving, worsening, or unchanged, or in a particular disease state. A record can be saved in memory indicating the assessment. The record may indicate the time period(s) that the assessment covers (i.e. corresponding to the time the bioelectrical signal was sensed), the relative amount of improvement or worsening, a metric characterizing the non-motor epileptiform bioelectrical activity, the conclusion of the assessment (e.g., improving, worsening, unchanged), and/or a diagnosis based on the assessment (e.g., mild cognitive impairment, pre-Alzheimer's disease, Alzheimer's disease), among other things. The record may be transmitted to another device, such as by being transmitted wirelessly from an implantable medical device to an external programmer A report may be displayed (e.g., on a screen or by printing on paper) detailing the assessment, such as by including any information from the record.

Figure 3:
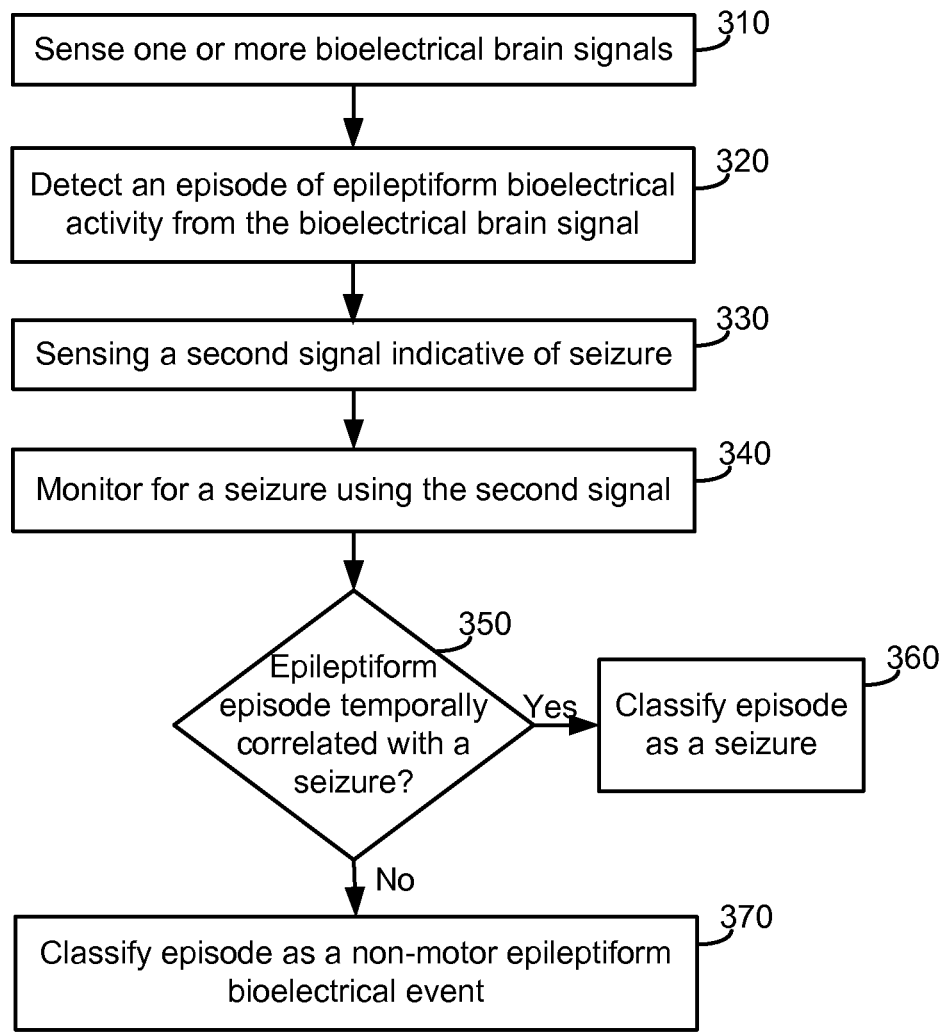
FIG. 3 is a flowchart for discriminating between a seizure and an episode of non-motor epileptiform bioelectrical activity.

Being that the present disclosure is directed to identifying non-motor epileptiform bioelectrical activity episodes, which have some bioelectrical resemblances to episodes of epileptic seizures, it may be useful to discriminate between non-motor epileptiform bioelectrical activity episodes and epileptic seizures. FIG. 3 illustrates a flowchart of a method 300 for discriminating between non-motor epileptiform bioelectrical activity episodes and epileptic seizures. The method 300 includes sensing 310 bioelectrical brain signals, which can be done in any manner. The method 300 further includes detecting 320 an episode of epileptiform bioelectrical activity from the bioelectrical brain signals. Detecting 320 the episode of epileptiform bioelectrical activity can be done in any manner, such as by the techniques referenced herein for detecting a non-motor epileptiform bioelectrical episode from a bioelectrical brain signal. Before, during, and/or after sensing 310 and detecting 320, a second signal can be sensed 330 and the second signal can be analyzed to monitor 340 for a seizure. It is noted that the monitoring 340 step may not detect any seizures, which as further explained herein may indicate that the patient has a non-motor epileptiform activity condition and not a seizure disorder. In some embodiments, the second signal is not sensed 330 and monitored 340 but rather the second signal is received from an input device (e.g., a patient programmer) indicating the occurrence of a seizure or is received from another source.

The sensed 330 second signal may be any signal indicative of a seizure that is different from the sensed 310 one or more bioelectrical brain signals. For example, the second signal may not be a bioelectrical brain signal. In some embodiments, the second signal is an accelerometer signal. An accelerometer can output a signal indicative of the forces to which the sensor is subject due to accelerations. If a patient is experiencing a seizure, then the patient may experience involuntary movement or loss of bodily control. A seizure may manifest as mild to violent shaking, a slump of the body, or other characteristic movement which can be perceivable by the accelerometer. For example, shaking can be identified in an accelerometer signal as rhythmic and abnormal changes in the signal, such as rapid fluctuations between positive and negative acceleration. A sensed 330 second signal may be indicative of a physiological activity, such as heart rate or breathing. An electrical cardiac signal indicative of heart rhythms can be sensed by electrodes. Some cardiac patterns can be indicative of a seizure, such as an increase in heart rate. An accelerometer can also detect heart rhythms and/or breathing patterns. An increasing in breathing rate can be indicative of a seizure. Electrodes can also measure the impedance across the chest of a patient, which can be indicative of breathing by the impedance increasing and decreasing with the expansion and deflation of the chest. A seizure can be detected based on the monitoring 340 of the second signal using these and other techniques.

The method 300 further includes determining 350 whether there is temporal correlation between one or more episodes of epileptiform bioelectrical activity and one or more seizures. An episode of epileptiform bioelectrical activity may be classified based on whether it is temporally correlated with a detected seizure. An episode of epileptiform bioelectrical activity may be classified 360 as a seizure if the episode of epileptiform bioelectrical activity is temporally correlated with the detected seizure (e.g., the episode temporally overlaps with the seizure and/or is temporally proximate the seizure), in which case the episode would fail to be non-motor epileptiform bioelectrical activity. An episode of epileptiform bioelectrical activity may be classified 370 as a non-motor epileptiform bioelectrical episode if the episode of epileptiform bioelectrical activity is not temporally correlated with a seizure. In some cases, an episode of epileptiform bioelectrical activity is not temporally correlated with a seizure when the episode does not temporally overlap with a seizure and/or is not temporally proximate a seizure (e.g., within a number of seconds).

In some embodiments, the total number of episodes of epileptiform bioelectrical activity classified 360 as a seizure is calculated. Likewise, the total number of episodes of epileptiform bioelectrical activity classified 370 as non-motor epileptiform bioelectrical episode can be calculated. In some embodiments, the rate of occurrence of classified 360 seizures and/or classified 370 non-motor epileptiform bioelectrical activity episodes can be used to diagnose a condition and/or to rule out a condition for a patient. Respective thresholds can be established for the total number, percentage of, rate of occurrence, or any other metric for characterizing a medical condition of the patient (e.g., any of the conditions referenced herein) as mild cognitive impairment, Alzheimer's disease, and/or a seizure disorder, among others. For example, if a patient has a threshold number of non-motor epileptiform bioelectrical activity episodes, then the patient's condition can be characterized as a cognitive disorder. If a patient has a threshold number of seizures, then the patient's condition can be characterized as a seizure disorder. Thresholds for characterizing a patient condition can also be set based on rates. For example, a cognitive disorder is declared if the rate of occurrence of non-motor epileptiform bioelectrical activity episodes exceeds a threshold and/or a seizure disorder is declared if the rate of occurrence of seizures exceeds a threshold. In some cases, the presence of seizures, such as a threshold number or rate of seizures, will rule out a cognitive disorder from being identified for a patient, regardless of the number or rate of non-motor epileptiform bioelectrical activity episodes the patent also experiences. However, the full scope of the present disclosure is not so limited.

Discrimination between a seizure and a non-motor epileptiform bioelectrical episode may be benefited by seizure detection techniques, such as those of commonly assigned U.S. Patent Application Publication No. 2010/0121215, filed on Apr. 29, 2009, by Giftakis et al., titled SEIZURE DETECTION ALGORITHM ADJUSTMENT, which is incorporated by reference herein in its entirety.

Figure 4:
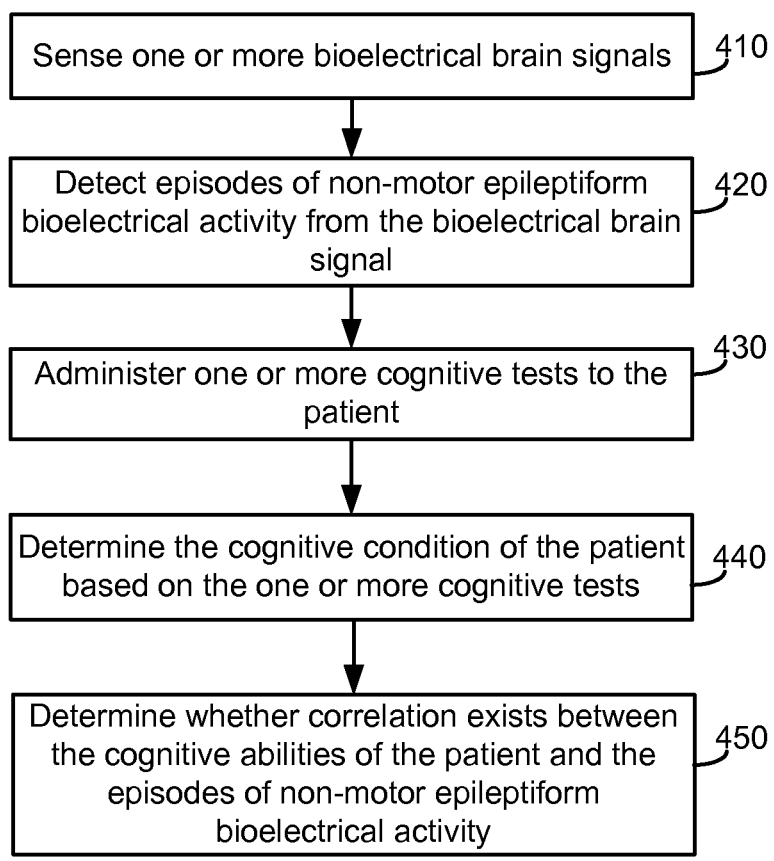
FIG. 4 is a flowchart for correlating non-motor epileptiform bioelectrical activity and a cognitive disorder of a patient.

In some embodiments, one or more cognitive tests are administered to the patient to further assess a cognitive disorder. A patient's performance on a cognitive test can be a second indicator of the cognitive disorder, which can corroborate or contradict the assessment of the cognitive disorder based on the non-motor epileptiform bioelectrical activity. FIG. 4 illustrates a flowchart of a method 400 for administering a cognitive test along with monitoring non-motor epileptiform bioelectrical activity. The method 400 includes sensing 410 one or more bioelectrical brain signals, which can be done in any manner. The method 400 further includes detecting 420 episodes of non-motor epileptiform bioelectrical activity from the one or more bioelectrical brain signals. Detecting 420 the episodes of non-motor epileptiform bioelectrical activity can be done in any manner, such as in any manner referenced herein.

Before, during, and/or after the sensing 410 and detecting 420 steps, one or more cognitive tests can be administered to the patient. The cognitive tests can be any test for assessing the memory, reasoning, concentration, comprehension, and/or any other cognitive abilities of the patient, for example. One or more tests may be administered by an external device, such as a programmer or a desktop computer. The tests may comprise a memory game testing whether a patient can be exposed to information and then recall the information at a later time. The tests may comprise a logical puzzle (e.g., completing a diagram), a word game (e.g., forming words from mixed letters), a spatial puzzle (e.g., a maze), and/or a knowledge test (e.g., answering questions testing the knowledge of a patient).

One or more scores may be generated based on the results of the patient's performance on the one or more cognitive tests. For example, a patient may receive a score on a ten point scale indicating the relative performance of the patient on the test. Multiple scores can be respectively generated for multiple cognitive tests administered over time, such as daily, weekly, or monthly.

The method 400 further includes determining 450 whether correlation exists between the cognitive disorder of the patient based on the cognitive tests and the episodes of non-motor epileptiform bioelectrical activity. Determining 450 whether correlation exists can include assessing whether the results of one or more cognitive tests indicate a similar cognitive disorder as the prevalence of the non-motor epileptiform bioelectrical activity would likewise suggest. For example, a cognitive test may indicate that the patient has diminished cognitive performance while a significant amount of non-motor epileptiform bioelectrical activity (e.g., as indicated by a relatively high number or rate of episodes) may likewise indicate a cognitive disorder associated with diminished cognitive performance. In this way, correlation can be determined 450 between poor cognitive performance and the significant non-motor epileptiform bioelectrical activity, corroborating the presence of a cognitive disorder. In some cases, a cognitive test may indicate that the patient as poor cognitive performance while a lack of non-motor epileptiform bioelectrical activity may then fail to correlate non-motor epileptiform bioelectrical activity with the declining cognitive performance (e.g., in which case the cognitive disorder may be unassociated with non-motor epileptiform bioelectrical activity). If a correlation between cognitive ability and prevalence of non-motor epileptiform bioelectrical activity is identified, then the non-motor epileptiform bioelectrical activity can be qualified or otherwise used as a biomarker for tracking the cognitive disorder, generating a report, and/or controlling a therapy. In some cases, if the cognitive test indicates diminished cognitive performance and the prevalence of non-motor epileptiform bioelectrical activity indicates the presence of a cognitive disorder, then therapy may be started or increased in intensity based on the dual assessment. If the cognitive test indicates improved cognitive performance and the prevalence of non-motor epileptiform bioelectrical activity indicates the absence of a cognitive disorder, then therapy may be stopped or decreased in intensity based on the dual assessment.

In some embodiments, determining 450 whether correlation exists between the cognitive abilities of the patient and the non-motor epileptiform bioelectrical activity can include trending the patient's performance on the cognitive tests and trending the non-motor epileptiform bioelectrical activity to determine whether the trends correlate. For example, a decline in the patient's performance on the cognitive tests over time (e.g., as measured by a standard score for each test) may be correlated with an increase in non-motor epileptiform bioelectrical activity over the same time, each of which may indicate a worsening cognitive disorder. An improvement in the patient's performance on the cognitive tests over time may be correlated with a decrease in non-motor epileptiform bioelectrical activity over the same time, each of which may indicate an improving cognitive disorder. Consistency in the patient's performance on the cognitive tests over time may be correlated with consistency in non-motor epileptiform bioelectrical activity over the same time, each of which may indicate an unchanging cognitive disorder. A decline in the patient's performance on the cognitive tests over time may then not correlate with steady or decreasing non-motor epileptiform bioelectrical activity over the same time, in which case the cognitive disorder may be unassociated with non-motor epileptiform bioelectrical activity. If a correlation in trends between cognitive ability and prevalence of non-motor epileptiform bioelectrical activity is identified, then the non-motor epileptiform bioelectrical activity can be qualified or otherwise used as a biomarker for tracking the cognitive disorder, generating a report, and/or controlling a therapy.

Statistical routines can be run on the cognitive performance test results and the prevalence of non-motor epileptiform bioelectrical activity to determine the degree of correlation between the cognitive abilities of the patient and the non-motor epileptiform bioelectrical activity. If there is a high degree of correlation between the cognitive abilities of the patient and the non-motor epileptiform bioelectrical activity, then the non-motor epileptiform bioelectrical activity may be qualified as a biomarker for the cognitive disorder of the patient or otherwise be associated with the cognitive disorder of the patient. If the cognitive disorder and the non-motor epileptiform bioelectrical activity are associated, the episodes can then be used as an indicator of the cognitive disorder of the patient, which can be used for tracking the cognitive disorder of the patient and/or controlling a therapy. For example, in some cases the non-motor epileptiform bioelectrical activity will not be used for tracking a cognitive disorder of the patient and/or controlling a therapy for a patient until the non-motor epileptiform bioelectrical activity are correlated with the cognitive abilities of the patient.

Figure 5:
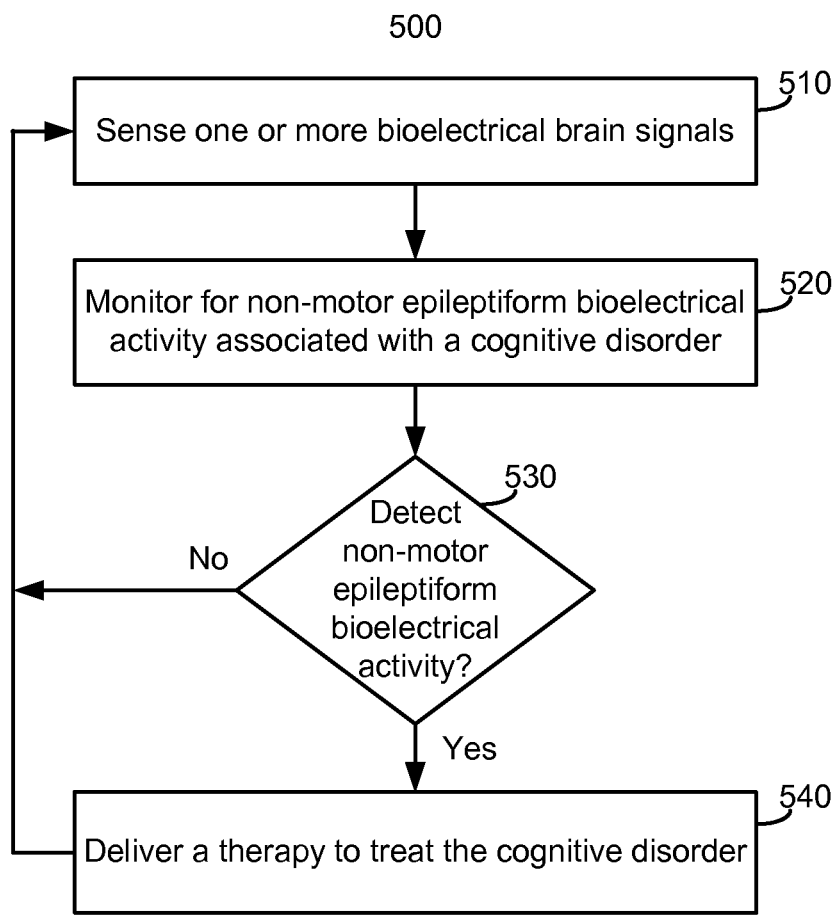
FIG. 5 is a flowchart for controlling a therapy based on assessment of a cognitive disorder using non-motor epileptiform bioelectrical activity.

FIG. 5 illustrates a flowchart of a method 500 for controlling a therapy based on an assessment of a cognitive disorder. The method 500 includes sensing 510 one or more bioelectrical brain signals, which can be done in any manner. The method 500 further includes monitoring 520 for non-motor epileptiform bioelectrical activity associated with a cognitive disorder using the one or more bioelectrical brain signals. Monitoring 520 can include running one or more sensed 510 bioelectrical brain signals through an event detection algorithm to detect one or more biomarkers indicative of non-motor epileptiform bioelectrical activity.

In some embodiments, if no non-motor epileptiform bioelectrical activity is detected 530, then sensing 510 and monitoring 520 continue without therapy delivery 540. However, if non-motor epileptiform bioelectrical activity is detected 530, then therapy is delivered 540 to treat the cognitive disorder. As discussed herein, non-motor epileptiform bioelectrical activity can be indicative of a cognitive disorder. Therefore, a cognitive disorder as evidenced by symptomatic non-motor epileptiform bioelectrical activity can be assessed to be uncontrolled and warranting of therapy delivery 540. In some embodiments, delivery of each pulse, group of pulses, or a continuous waveform is triggered based on the detection 530 of non-motor epileptiform bioelectrical activity (e.g., as an episode). In some embodiments, delivery 540 of a drug is triggered based on the detection 530 of non-motor epileptiform bioelectrical activity. Such delivery can include prescription, administration, and/or infusion of a drug, and can be administered in the presence or absence of electrical stimulation.

In some embodiments, therapy delivery 540 can be triggered for each detection 530 of non-motor epileptiform bioelectrical activity. For example, if an episode of non-motor epileptiform bioelectrical activity is identified from the monitoring 520, a therapy may immediately be delivered 540. The therapy may be delivered 540 to suppress the detected 530 non-motor epileptiform bioelectrical activity, such as to intervene and end the episode. In some cases, the therapy may be delivered 540 upon the detection of a first non-motor epileptiform bioelectrical episode to proactively avoid a second episode (e.g., where the conditions that lead to the first episode may increase the likelihood of a second episode occurring in proximity to the first episode).

In various embodiments of the method 500, as long as no epileptiform bioelectrical activity is detected 530, then no therapy is delivered 540. In some cases, a loop through the sensing 510, monitoring 520, and detecting 530 steps may recognize non-motor epileptiform bioelectrical activity, and as such therapy may be delivered 540 based on the detection 530. The method 500 then loops back through these same steps of sensing 510, monitoring 520, and detecting 530. If in the later monitoring 520 step the non-motor epileptiform bioelectrical activity is no longer detected 530, then the delivery 540 of the therapy can be stopped. As such, in some embodiments, therapy is initiated in response to non-motor epileptiform bioelectrical activity and is stopped when the non-motor epileptiform bioelectrical activity ceases. In some other embodiments, therapy is initiated in response to non-motor epileptiform bioelectrical activity and then continues for a predetermined amount of time (e.g., according to a duty cycle) even if the non-motor epileptiform bioelectrical activity stops. It is noted that sensing 510 and monitoring 520 may be performed continuously, such that sensing 510 and monitoring 520 are performed during therapy delivery 540, however not all embodiments are so limited.

It is noted that the methods 100 and 500 can correspond to the same embodiments, with the flowcharts and discussions of FIGS. 1 and 5 highlighting different aspects of controlling therapy. It is also noted that not all embodiments in practice will perform each of the steps of the methods presented herein, and modifications to the methods are contemplated, whether by omitting and/or adding steps. Each of the methods discussed herein can be fully or partially implemented in control circuitry of an implantable medical device (e.g., a neurostimulator configured for DBS) and/or an external device.

Degenerative cognitive disorders associated with non-motor epileptiform bioelectrical activity can be characterized by inappropriate bioelectrical brain activity within one or more brain structures. Accordingly, for at least some patients, reducing the bioelectrical activity level within various brain areas (e.g., the hippocampus) may reduce problematic bioelectrical activity such as non-motor epileptiform bioelectrical activity and therefore may be desirable for managing a degenerative cognitive disorder. The reduced bioelectrical activity level within the stimulated brain structure(s) may help mitigate symptoms of the non-motor epileptiform bioelectrical activity, such as by lowering the likelihood of occurrence, duration, and/or frequency of non-motor epileptiform bioelectrical activity episodes and minimizing the damage from the episodes or from the brain's response to the episodes. Deep brain stimulation is one option for therapeutically addressing non-motor epileptiform bioelectrical activity by lowering the activity within the problematic brain area, suppressing non-motor epileptiform bioelectrical activity, and/or disrupting intrinsic bioelectrical brain patterns associated with non-motor epileptiform bioelectrical activity. For example, a lead can be implanted with one or more electrodes contacting the temporal structure, hippocampus, or other brain area associated with non-motor epileptiform bioelectrical activity and targeted for stimulation therapy. Electrical stimulation delivered from the one or more electrodes can change the intrinsic bioelectrical electrical activity of the targeted brain area.

In some cases, DBS can therapeutically treat a cognitive disorder by suppressing non-motor epileptiform bioelectrical activity, thereby reducing the intensity, duration, and/or occurrence of episodes of non-motor epileptiform bioelectrical activity. Suppression therapy may include a reduction effect on bioelectrical activity in various embodiments, such as reducing all or some frequencies of bioelectrical oscillation in a targeted brain area and/or the amplitude of intrinsic bioelectrical brain activity. Such a reduction in intrinsic bioelectrical brain activity may prevent or reduce non-motor epileptiform bioelectrical activity by lowering the excitability of brain tissue that could lead to non-motor epileptiform bioelectrical activity and/or breaking up the patterns associated with non-motor epileptiform bioelectrical activity. Therapy delivery for bioelectrical activity suppression can comprise pulses delivered at 80 Hz or greater, and 100 Hz or greater, and 80-140 Hz in some embodiments, however not all embodiments are so limited.

In various embodiments, changing a stimulation parameter will comprise increasing a stimulation energy parameter in an effort to bring about an intended therapeutic results, such as reduction in non-motor epileptiform bioelectrical activity (e.g., whether by suppression or disruption of non-motor epileptiform bioelectrical activity). Energy parameters can include pulse amplitude, width, and frequency, among other parameters. In some embodiments, an assessment is made as to whether the therapy delivery is reducing non-motor epileptiform bioelectrical activity (e.g., reducing the intensity, duration, and/or frequency of occurrence of episodes). For example, during and/or after therapy delivery, bioelectrical activity of the patient's brain can be sensed to determine whether the level of non-motor epileptiform bioelectrical activity (e.g., as measured by episode intensity, duration, frequency, and/or some other metric) has increased, decreased, or stayed the same as compared to the untreated level non-motor epileptiform bioelectrical activity and/or a previous level of non-motor epileptiform bioelectrical activity sensed in association with therapy delivery using different therapy parameters. If the therapy parameters (e.g., initial or most recently used therapy parameters) did not reduce non-motor epileptiform bioelectrical activity, then other therapy parameters can be used for therapy delivery. In some cases, a scan of therapy parameters can be performed by changing (e.g., incrementing pulse amplitude) therapy parameters and monitoring non-motor epileptiform bioelectrical activity until therapy parameters are identified that reduce non-motor epileptiform bioelectrical activity below a threshold level. Repeated failure to reduce non-motor epileptiform bioelectrical activity by stimulation can trigger repeated increasing of stimulation energy or another parameter of therapy by changing the therapy stimulation parameter in an incremental manner until the intended therapeutic result (e.g., reduced or eliminated non-motor epileptiform bioelectrical activity) is achieved. Other changes can be performed to scan for efficacious therapy parameters. In some embodiments, an electrical stimulation therapy will only be delivered if a test of delivering the therapy can show that the therapy reduces non-motor epileptiform bioelectrical activity to a satisfactory degree (e.g., below a threshold).

Figure 6:
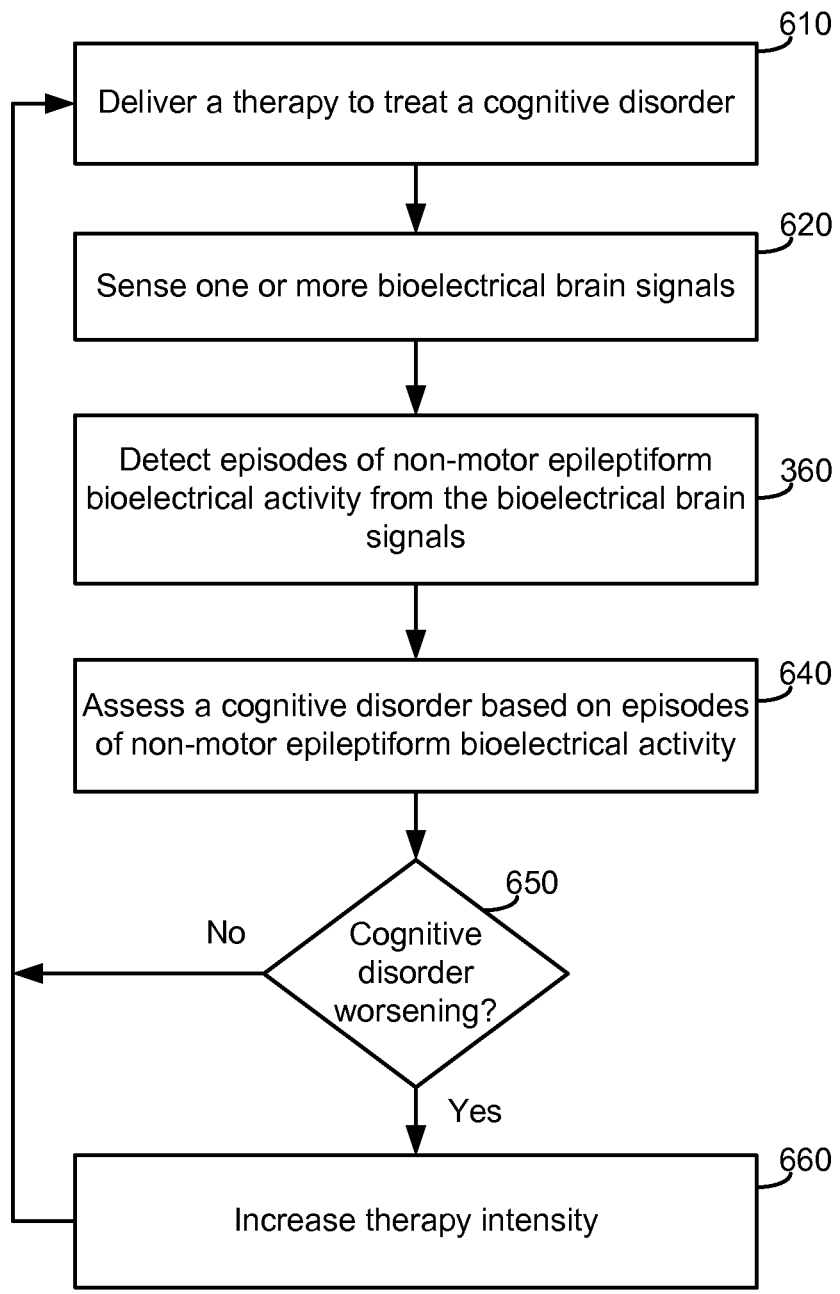
FIG. 6 is a flowchart for controlling a therapy based on assessment of a cognitive disorder using non-motor epileptiform bioelectrical activity.

FIG. 6 illustrates a flowchart of a method 600 for controlling a therapy based on an assessment of a cognitive disorder. The method 600 includes delivering 610 a therapy to treat a cognitive disorder. The therapy may be any type of therapy referenced herein, and may treat the underlying cognitive disorder and/or may attempt to address one or more symptoms of the cognitive disorder. It is noted the delivery 610 of the therapy may be performed throughout the method 600, overlapping with one, multiple, or all of the other steps. The method 600 includes sensing 620 one or more bioelectrical brain signals. The method 600 further includes detecting 630 non-motor epileptiform bioelectrical activity from the one or more bioelectrical brain signals. Detecting 630 the non-motor epileptiform bioelectrical activity can be done in any manner, such as by using the techniques disclosed herein.

Based on the detection 630 of non-motor epileptiform bioelectrical activity, the cognitive disorder can be assessed 640. Assessment 640 of the cognitive disorder can be performed various ways, such as in the manner of FIG. 2 for example. If the cognitive disorder is assessed 640 to be worsening 650, then the intensity of the delivered 610 therapy can be increased. In the case of an electrical stimulation therapy, increasing 660 the intensity of the therapy can include increasing the energy level of the electrical stimulation (voltage or current), which can include increasing the amplitude, pulse width, pulse frequency, a burst length, a burst frequency, and/or other energy parameter of the delivered 610 electrical stimulation, among other things. In some embodiments, a duty cycle or duration of stimulation can be lengthened to increase 660 the therapy intensity. In some embodiments, the electrode or electrode combination used for stimulation delivery can be switched to a different electrode or electrode combination if the cognitive disorder is worsening 650. In the case of a drug therapy, increasing 660 the intensity of the therapy can include increasing the concentration, potency, frequency of delivery, and/or amount of the drug delivered 610, among other things. If the cognitive disorder is not worsening 660, then the method 600 continues delivering 610 the therapy using the current therapy parameters, however various other actions could be taken in various embodiments.

Various embodiments configured to carry out the method 600 of FIG. 6 could implement a variety of different actions based on the assessment 640 of the cognitive disorder. In some cases, the assessment 640 may determine whether the cognitive disorder is improving, unchanging, or worsening (e.g., based on whether the non-motor epileptiform bioelectrical activity is decreasing, unchanging, or increasing, respectively). The flowchart of FIG. 6 shows the method 600 increasing 660 therapy intensity based on a worsening 650 cognitive disorder. In some embodiments, the therapy intensity is likewise increased 660 if the assessment 640 indicates that the cognitive disorder is unchanged or otherwise not improving. In such cases, the current therapy parameters may be deemed ineffective if they fail to improve the cognitive disorder (e.g., by lowering the non-motor epileptiform bioelectrical activity). In some other cases, at least stabilizing the cognitive disorder as evidenced by consistent (and not increasing) non-motor epileptiform bioelectrical activity is an at least partially successful result for therapy and the therapy parameters may accordingly be deemed acceptable and not in need of changing. However, in some other embodiments an improvement in the cognitive disorder may be expected and the therapy will be titrated until parameters are identified that can decrease non-motor epileptiform bioelectrical activity. In some embodiments, therapy intensity may be decreased if the assessment 640 indicates that the cognitive disorder is improving (e.g., evidenced by decreasing non-motor epileptiform bioelectrical activity). In such cases, decreasing the therapy intensity can help avoid therapy side effects and/or preserve energy or a drug by delivering only as much therapy as needed to achieve satisfactory results. However, in various cases large decreases in non-motor epileptiform bioelectrical activity are sought, and in such cases therapy intensity may be maintained to maintain or further drive down the non-motor epileptiform bioelectrical activity.

While the flowchart of FIG. 6 shows increasing a stimulation parameter to increase therapy intensity, other changes to a stimulation protocol could additionally or alternatively be made based on an assessment of a cognitive disorder (e.g., such as whether characteristic non-motor epileptiform bioelectrical activity is being reduced by therapy). In some embodiments, different stimulation parameter levels can be scanned to identify a set of stimulation parameters that is effective in addressing the cognitive disorder. For example, an amplitude stimulation parameter can be scanned by incrementing the stimulation amplitude (e.g., voltage or current) until an amplitude level is reached that reduces non-motor epileptiform bioelectrical activity (e.g. as determined by detecting less or no non-motor epileptiform bioelectrical activity). The parameters that can be changed include pulse amplitudes, the amount of charge delivered in each pulse, pulse widths, frequency (e.g., the frequency at which pulses within a burst are delivered), burst length, burst frequency, waveform amplitude, and a duty cycle, among other stimulation parameters.

While the flowchart of FIG. 6 shows increasing a stimulation parameter to increase therapy intensity, other changes to a stimulation protocol could additionally or alternatively be made based on an assessment of a cognitive disorder (e.g., such as whether characteristic non-motor epileptiform bioelectrical activity is being reduced by therapy). In various embodiments, one or more electrodes used for delivering the stimulation therapy can be changed (e.g., if a previous one or more electrodes were ineffective at addressing the non-motor epileptiform bioelectrical activity) until one or more electrodes are identified that are effective in addressing cognitive disorder (e.g., by reducing the characteristic non-motor epileptiform bioelectrical activity). An electrode switch can be performed repeatedly until such an electrode combination is found, an assessment of the cognitive condition being completed for each electrode combination.

In some embodiments, one or more stimulation parameters can be changed based on feedback, such as an assessment of the cognitive disorder. For example, various embodiments can include delivering electrical stimulation, monitoring of the bioelectrical activity of the patient (e.g., monitoring for non-motor epileptiform bioelectrical activity), and changing a stimulation parameter in real-time based on whether the previously used stimulation parameter reduced non-motor epileptiform bioelectrical activity.

Various embodiments of this disclosure concern the delivery of a cycled therapy, where stimulation is cyclically turned on and off, such as alternating periods of one minute of stimulation delivery (stimulation on) and one minute of no stimulation (stimulation off). Other cycle times are also contemplated. In some cases, the benefits of therapy persist during the therapy-off periods in a carryover effect, which is referred to as a washout period. For example, a cycle of stimulation delivery may suppress non-motor epileptiform bioelectrical activity and the suppression may persist for a minute or more during a washout period, while the suppression effect eventually subsides and the non-motor epileptiform bioelectrical activity returns (e.g., to a pre-stimulation level). Some cycled therapy embodiments resume stimulation following the expiration of a timer, while some other embodiments monitor the level of non-motor epileptiform bioelectrical activity during the washout period and resume therapy delivery when the non-motor epileptiform bioelectrical activity reappears.

While the various embodiments of FIGS. 1-6 have principally concerned assessing a cognitive disorder and controlling therapy, based on detection of non-motor epileptiform bioelectrical activity, some embodiments can further concern assessing the cognitive disorder and controlling therapy based on detection of slowing of bioelectrical brain activity. It may be the case that excessive non-motor epileptiform bioelectrical activity over a long period of time may transition to slowing of bioelectrical activity in the brain relative to the normal bioelectrical activity. In particular, the level of bioelectrical brain activity in some areas of the brain may be significantly lower than a baseline level (e.g., as representative of a healthy brain state) as a cognitive disorder reaches advanced stages, such as in Alzheimer's disease. Slowing, associated with advanced stages of cognitive disorders, can be characterized by temporal short waves, reduction in alpha frequency oscillations, arrhythmic (disorganized) 2-3 Hz waves, reduction in bioelectrical signal amplitude (e.g., below baseline), and/or bisynchronous slow waves (i.e. in both hemispheres), depending on the patient. These characteristics can be used as biomarkers for detecting slowing from a bioelectrical brain signal (e.g., by an algorithm applying one or more of these characteristics as criteria for detection of slowing).

A stimulation therapy to address slowing of bioelectrical activity associated with an advanced cognitive disorder can include an excitatory low frequency (e.g., 1-80 Hz) pulse therapy. While a therapy that suppresses bioelectrical brain activity (e.g., non-motor epileptiform bioelectrical activity in particular) may be beneficial during an early stage of a cognitive disorder, such suppressive therapy may be counterproductive if the cognitive disorder has advanced to brain slowing, at which stage an excitatory therapy may be preferred. Likewise, if a patient is experiencing non-motor epileptiform bioelectrical activity, then an excitatory therapy may promote non-motor epileptiform bioelectrical activity. As such, some embodiments may preferably assess a cognitive disorder, determine whether non-motor epileptiform bioelectrical activity or brain slowing is present, and then deliver a suppressive or excitatory therapy respectively.

Figure 7:
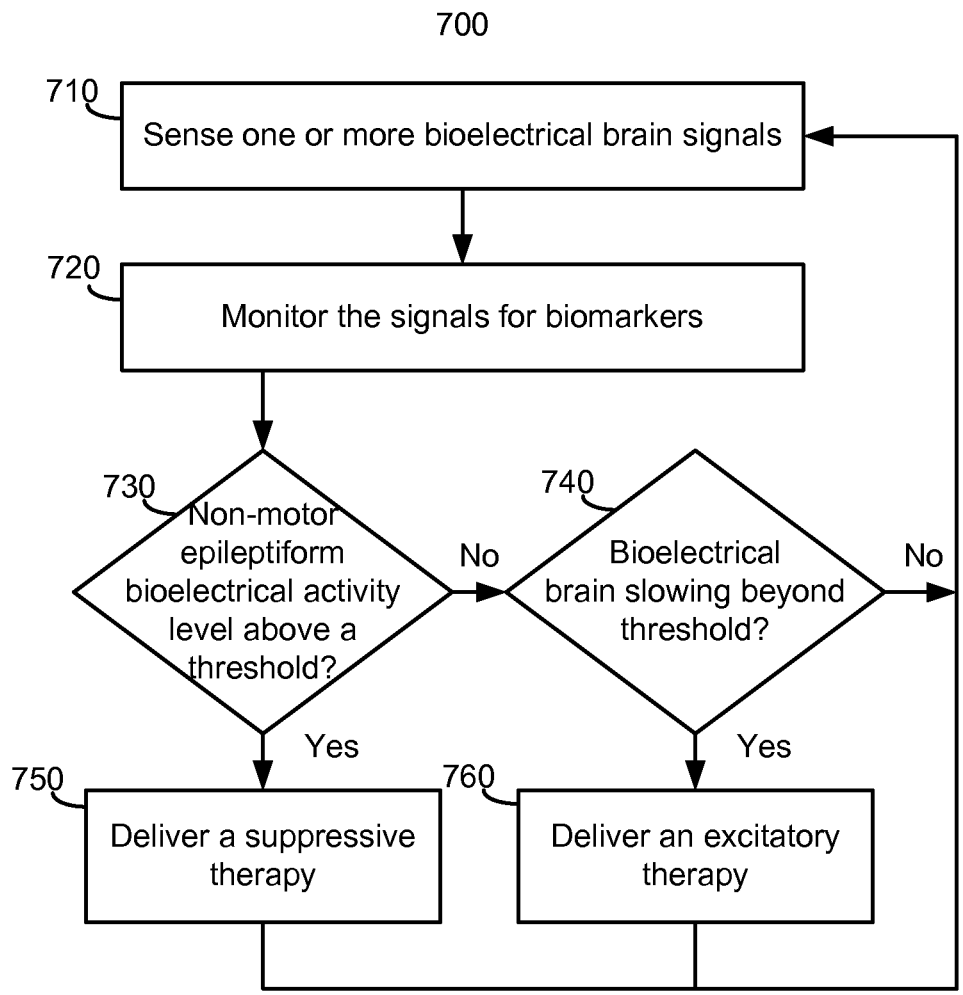
FIG. 7 is a flowchart for controlling managing suppressive and excitatory therapies.

FIG. 7 illustrates a flowchart of a method 700 for assessing a cognitive disorder of a patient and controlling a therapy based on non-motor epileptiform bioelectrical activity. In particular, the method 700 assesses whether the patient's condition is associated with non-motor epileptiform bioelectrical activity or bioelectrical slowing and provides therapy delivery in either scenario. The method 700 includes sensing 710 one or more bioelectrical brain signals 710. The method 700 further includes monitoring 720 the sensed 720 signals for biomarkers. The method 700 may monitor for a first biomarker and a second biomarker, where the first biomarker is indicative of non-motor epileptiform bioelectrical activity and the second biomarker is indicative of brain slowing.

Detection of non-motor epileptiform bioelectrical activity is discussed above. Bioelectrical brain slowing may be identified by lack of normal, high frequency oscillations in the bioelectrical brain signal, disrupted frequency matching of oscillations between various regions of the brain which may disrupt normal frequency matching of oscillations of the bioelectrical brain signal across brain areas, reduced phase locking of oscillations which may prohibit phase locking of oscillations needed for normal mental function, and/or pathological synchronization across regions of the brain.

In an arousal state unassociated with brain slowing (e.g., indicating an acceptable or improved cognitive state), the bioelectrical signals from the brain can exhibit a gamma frequency oscillation and/or a beta frequency oscillation. In some cases, a bioelectrical brain signal that exhibits a oscillation in a theta band may be indicative of a relatively low arousal state and accordingly brain slowing, where excitatory therapy may be desirable. In some cases, an increase in activity in the theta band may be indicative of a relatively low arousal state. A bioelectrical brain signal indicative of a relatively high arousal state in the brain may be defined by a bioelectrical brain signal exhibiting relatively small amplitude values and relatively high frequency values compared to a bioelectrical brain signal indicative of a relatively low arousal state. Consequently, in some cases, arousal state information (not associated with brain slowing) may include predefined threshold values for amplitude and/or frequency of a bioelectrical brain signal that correlate to a relatively high arousal state and/or to a relatively low arousal state. Upon assessment of the cognitive disorder based on the detection of different biomarkers, different therapeutic actions can be taken.

In some cases, one or more signals are sensed 710 over a period of time (e.g., an hour or a day). The number of detected biomarkers can be aggregated to determine whether a total number, rate of detection, or some other parameter crosses a first threshold. For example, a total number of non-motor epileptiform bioelectrical activity episodes, rate of occurrence of non-motor epileptiform bioelectrical activity episodes, or some other aggregate parameter of non-motor epileptiform bioelectrical activity episodes could be calculated for a time period and then compared to a non-motor epileptiform bioelectrical activity threshold (as the first threshold 730). The first threshold can represent the presence of a cognitive disorder associated with abnormally excessive bioelectrical activity. Excessive amounts or rates of non-motor epileptiform bioelectrical activity can exceed the first threshold 730. If the first threshold 730 is passed, then suppressive therapy can be delivered 750. Suppressive therapy, as discussed herein, can attempt to preempt, abolish, or otherwise reduce non-motor epileptiform bioelectrical activity, such as by disrupting these patterns.

If insufficient non-motor epileptiform bioelectrical activity is present to exceed the first threshold 730, then brain slowing can be assessed and an excitatory therapy can be delivered 760 is needed. The second threshold 740 can represent an abnormal amount of brain slowing. Brain slowing can be quantified in various ways, such as by aggregating the number of brain slowing episodes, determine the rate of brain slowing episodes, determining a percentage of brain slowing episodes as compared to a total of all episodes (including seizure episodes, non-motor epileptiform episodes, etc.), and determining the degree of brain slowing (e.g., the reduction in bioelectrical amplitude, frequency, or phase locking relative to a baseline). A second threshold can represent an unacceptable level of brain slowing, where if a parameter measuring bioelectrical brain slowing passes the second threshold 740, the excitatory therapy can be delivered 760. Although a second threshold is used for assessing slowing, brain slowing could be assessed in other ways, such as comparison to absolute values, ranges, or other indicators of slowing. Excitatory therapy can attempt to promote states of arousal, where in arousal the brain is in a better state and symptoms of the cognitive disorder are diminished as compared to a slowing brain state. A parameter of intensity or other aspect of the excitatory therapy can be adjusted in the same manner as any other therapy described herein, such as by changing stimulation amplitude, pulse frequency, pulse width, and/or stimulation electrode(s) until an efficacious therapeutic effect is identified (e.g., arousal from brain slowing).

In some embodiments, a second indicator could corroborate bioelectrical slowing of the brain. In some cases, a cognitive test can be administered to the patient to test the cognitive abilities of the patient as a second indicator, such as in the manner described in FIG. 4. In various cases, the state of brain slowing is a more advanced stage of a degenerative cognitive disease (e.g., as compared to a state characterized by non-motor epileptiform bioelectrical activity). Lower scores on a cognitive test may corroborate the bioelectrical indication of brain slowing. As such, each of the method 400 and options discussed in connection with FIG. 4 can be applied to identifying a correlation between bioelectrical brain slowing and cognitive ability (in addition to, or instead of, identifying correlation between non-motor epileptiform bioelectrical activity and cognitive ability), including diagnosing a condition, tracking a degenerative cognitive disease, and controlling a therapy. In some cases, a therapy addressing brain slowing may only be delivered if a correlation between bioelectrical brain slowing and decreased cognitive ability is identified. Likewise, the method 300 and options discussed in connection with FIG. 3 can be applied to classifying an episode of bioelectrical brain slowing by receiving a physical indicator of brain slowing corroborating the bioelectrical brain slowing (e.g., by an accelerometer showing diminished physical activity and/or an input from a programmer reporting that an episode of cognitive difficulty was experienced).

An excitatory therapy may be an electrical stimulation therapy that causes a state of arousal in the patient's brain. In various embodiments, the electrical stimulation may induce a relatively high arousal state (e.g., as characterized by a relatively high amount of electrical activity sensed in a portion of the brain) in comparison to a relatively low arousal state of the brain that may exist before delivery of electrical stimulation (e.g., as characterized by a relatively low amount of electrical activity sensed in the portion of the brain). A relatively high arousal state may result in improved cognitive functions because the patient may be more engaged with, attentive to, and/or vigilant with respect to the surrounding environment and stimuli.

The particular parameter values that define the electrical stimulation that activates an arousal neural network in a brain of a patient in order to treat a cognitive disorder (e.g., the amplitude or magnitude of the stimulation signals, the duration of each signal, the waveform of the stimuli, the frequency of the signals, and the like) may be specific for the particular target stimulation site. In addition, the particular parameter values may be specific to the particular patient and to the particular patient disorder. Excitatory stimulation therapies can have a frequency in a range of about 50 Hz to about 250 Hz, a voltage of about 0.1 volts to about 10.5 volts, and a pulse width of about 60 microseconds to about 450 microseconds, however the present disclosure is not so limited.

Techniques for identifying brain slowing and stimulating to promote arousal is discussed in commonly assigned U.S. patent application Ser. No. 13/288,797, filed on Nov. 11, 2011, by Nelson et al., titled AROUSAL STATE MODULATION WITH ELECTRICAL STIMULATION, which is incorporated by reference herein in its entirety.

The techniques disclosed herein can employ a supervised machine learning algorithm (e.g., utilizing a support vector machine or another artificial neural network) to develop one or more discriminators for detecting different brain states. For example, a first brain state can be characterized by having non-motor epileptiform bioelectrical activity and a second state can be characterized by not having non-motor epileptiform bioelectrical activity. Such a second state may correspond to a baseline or healthy brain state. A third brain state corresponding to bioelectrical brain slowing may also be detected. The detection of the different brain states can be automated based on the discriminators, such as for automatic detection by control circuitry.

In implementing such a supervised machine learning technique, control circuitry can receive bioelectrical signals (e.g., a LFP signal sensed from the hippocampus) that represent multiple episodes of different patient states (e.g., presence and absence of non-motor epileptiform bioelectrical activity in different states) and extract characteristics from the signals. A clinician can review the extracted information (e.g., a LFP trace or a spectrogram) to determine at which times the patient had the different states. For example, a clinician can look at collected data to identify periods showing epileptiform bioelectrical activity and periods without epileptiform bioelectrical activity and annotate the data accordingly. These clinician assessed brain state determinations can be temporally associated with the extracted signal characteristics. The extracted characteristics and brain state information can be used to generate a classification boundary delineating a first brain state (e.g., a non-motor epileptiform bioelectrical activity episode) and a second brain state (e.g., having no epileptiform bioelectrical activity). A boundary for a third brain state (e.g., correspond to brain slowing) could also be generated. A classification boundary can also be set delineating additional patient states, such as a non-motor epileptiform and non-epileptiform brain states, or non-motor epileptiform and epileptiform brain states. Examples of signal characteristics that can be extracted from a sensed signal include a morphology of the signal (e.g., amplitude, slope, frequency, peak value, trough value, or other traits of the signal), the spectral characteristics of the signal (e.g., frequency band power level, a ratio of power levels, and the like), and/or any other signal characteristics referenced herein, for example.

The boundary can be formed in feature space using a supervised machine learning algorithm. Feature space plots samples in n-dimensional space, the dimensions being determined by the number of features used to describe the pattern. A feature is a characteristic of a signal parameter (e.g., indicating suppression or after-discharge). Each feature of feature space defines an axis, such that the values of a feature vector (e.g., parameter data plotted in feature space for one brain state instance) indicate the coordinates of a point within the feature space. A feature vector is a vector defined by two or more feature values indicative of respective parameters. A feature vector can be mapped to a point within feature space based on the values of the features in the feature vector. Each feature vector defines a point in feature space that a support vector machine implemented by a computing device can use to classify data. Each data point feature vector is a quantitative representation of the monitored feature values for a given time slice (e.g., a short window of time) and each feature vector defines a data point in the feature space that can be used, together with other feature vectors as data points, to generate a boundary or establish some other relationship (e.g., to be used to discriminate between non-motor epileptiform and non-epileptiform baseline states).

Training data can initially be used during a training phase to populate feature space and determine a boundary based on known occurrences of the different patient states. The occurrences of the different patient states may be known because, as described above, they are evaluated by a clinician. For example, a clinician can review data of multiple episodes (e.g., representing samplings of non-motor epileptiform and non-epileptiform states). A brain state indication may then be associated with corresponding data segments or signal characteristic levels (e.g., RMS, spectral energy) and input into a computing device.

A boundary can be set within feature space delineating the feature vectors of the different patient states. Such a process can then train the algorithm by setting the linear discriminate to differentiate different patient states based on subsequently sensed data. Parameter information can be extracted from the later sensed signal and compared to the boundary to determine whether the patient is in the first brain state (e.g., higher than baseline showing epileptiform bioelectrical activity) or the second brain state (e.g., similar to baseline with no epileptiform bioelectrical activity) based on which side of the boundary or boundaries the subsequent data (e.g., in the form of a feature vector) would lie in feature space.

Training data feature values can be based on data from one particular patient to be used in classifying future brain states for the particular patient or for classifying future brain states of a different patient. In some cases, feature values are based on more than one patient and could be used in classifying future brain states for one or more patients.

Figure 8:
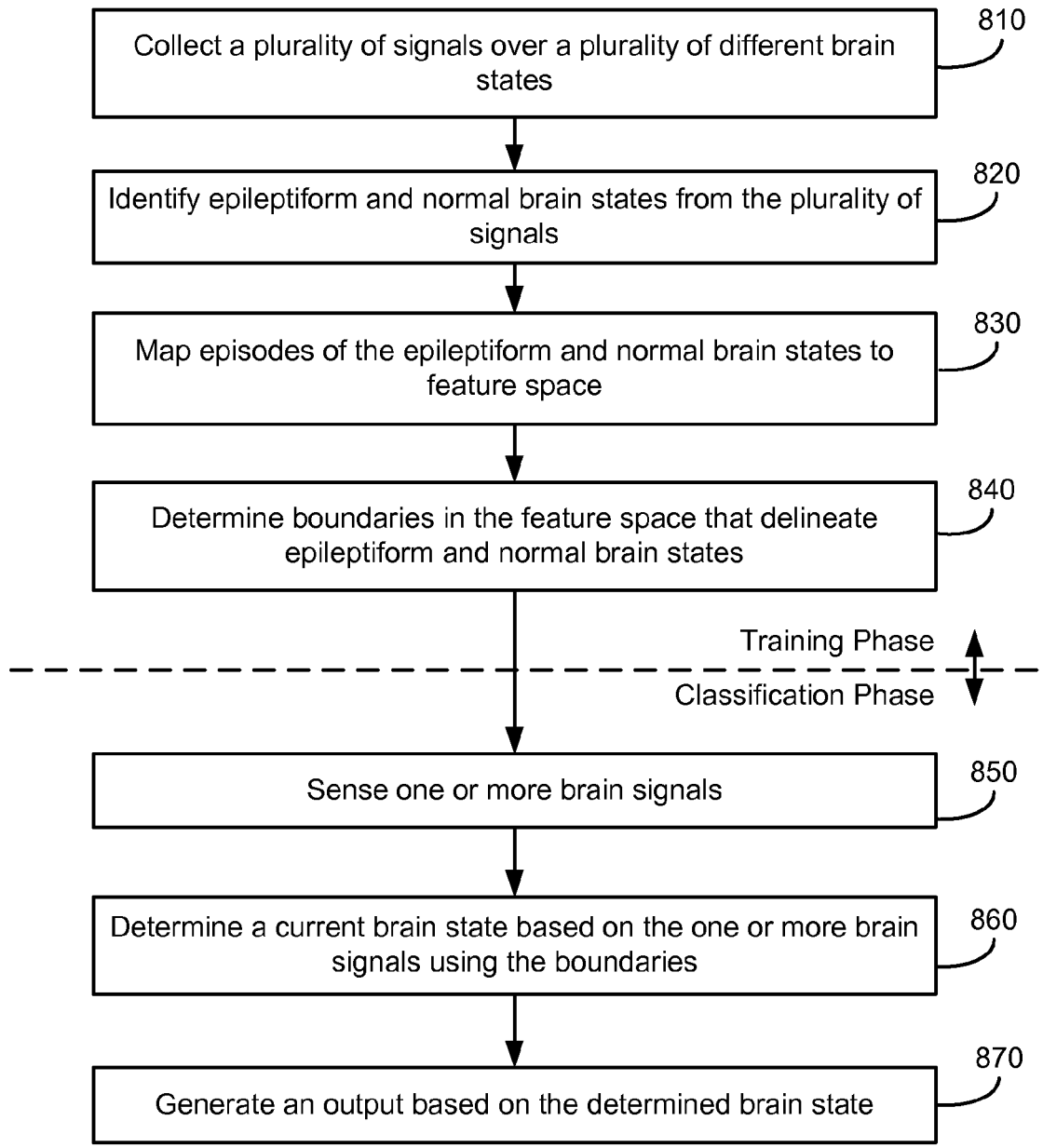
FIG. 8 is a flowchart for identifying brain states.

FIG. 8 illustrates a flow chart for a method 800 for determining a boundary that can be used in classification of a brain state and then monitoring the brain state of a patient. The method 800 includes collecting 810 a plurality of signals over a plurality of different brain states. The brain states can be baseline (no epileptiform bioelectrical activity) and non-motor epileptiform bioelectrical activity states, however additional or alternative brain states could be used (e.g., brain slowing). Collecting 810 in this manner may be done in the same manner of the sensing 110 one or more bioelectrical brain signals as referenced elsewhere herein. Collecting 810 can include storing the signal data in memory.

The method 800 further includes identifying 820 non-motor epileptiform and normal (i.e. non-epileptiform) brain states from the plurality of different signals. The brain states may be identified based on a characteristic of a LFP signal and/or spectrogram as discussed herein. The episodes may be manually noted by a clinician viewing the data and making input in a computing device or the identification of the episodes may be partially or fully automated by control circuitry. A normal baseline state may be identified based on a LFP signal and/or spectrogram not changing for a predetermined amount of time and being recognized as not containing abnormal bioelectrical events. For each of the episode identifications 820, the bioelectrical parameter levels sensed at that time can be noted.

Based on these bioelectrical parameter levels associated with the different identified 820 brain states, control circuitry can map 830 episodes of the brain states to feature space. Mapping 830 in this way can generate a feature space plot of episodic feature vectors, with one or more parameters being used for axes in feature space. One or more boundaries may be determined 840 in the feature space using control circuitry, the boundaries delineating the baseline (normal, non-epileptiform) and non-motor epileptiform bioelectrical activity brain states. For example, a baseline (normal, non-epileptiform) brain state may be on one side of a boundary while a non-motor epileptiform bioelectrical activity brain state may be on the other side of the boundary, the control circuitry setting the boundary in the separation space between different groupings of feature vectors of common brain states. A boundary may be set manually by a clinician by recognizing groupings of feature vectors of common brain states and setting a boundary within the separation between the different groupings.

Collecting 810, identify 820, mapping 830, and determining 840 comprise an initial training phase. Once the one or more boundaries are determined 840, the boundaries may be used in a classification phase that can classify subsequent patient brain states based on incoming information (e.g., brain state discrimination in real-time). The classification phase can include sensing 850 one or more bioelectrical brain signals. Characteristics of the signals may be extracted from the sensed 850 signals in the same manner as the identifying 820 brain states step, although the use of different analysis circuitry and/or techniques for the different phases is contemplated. In any case, a current brain state of a patient may be determined 860 based on one or more boundaries and the one or more signals, the boundary serving as a brain state threshold. The current patient state may be determined 860 by control circuitry running a linear discriminant algorithm which can determine on which side(s) of the one or more boundaries a current feature vector is, the current feature vector derived from the one or more sensed 850 signals.

An output may be generated 870 based on the determined 860 brain state. The output may be any output referenced herein, including initiating or increasing therapy delivery (e.g., in the case of an non-motor epileptiform bioelectrical activity episode), stopping therapy or decreasing therapy intensity (e.g., in the case of no epileptiform bioelectrical activity), maintaining therapy (e.g., in the case of an non-motor epileptiform bioelectrical activity episode), alerting a patient and/or clinician to the brain state, and/or storing data characterizing the brain state episode of the patient.

In various embodiments, the training phase can be used without the classification phase and the classification phase can be used without the training phase. For example, a boundary may be set using a technique that is substantively different from the training phase of the method 800 and that boundary may be used to classify brain state episodes. Also, the training phase may determine 840 a boundary that is used in a substantively different way as the classification phase of the method 800 to classify a patient state or for some other purpose. It is noted that the classification phase may be performed in accordance to any of techniques discussed in connection with FIGS. 1-7.

Aspects of detecting various patient states and using feature space, among other things, that can be applied to the present subject matter are disclosed in commonly assigned U.S. Pat. App. No. 2010/0280335 to Carlson et al., which is titled "PATIENT STATE DETECTION BASED ON SUPERVISED MACHINE LEARNING BASED ALGORITHM" filed Nov. 4, 2010; and U.S. Pat. App. No. 2010/0280334 to Carlson et al., which is titled "PATIENT STATE DETECTION BASED ON SUPPORT VECTOR MACHINE BASED ALGORITHM" filed Nov. 4, 2010, which are each incorporated herein by reference in their entireties.

Monitoring of bioelectrical activity may be benefited by the ability to sense bioelectrical activity and detect brain events while electrical stimulation is being delivered. Sensing of brain signals and detecting brain events in the presence of electrical stimulation is discussed in commonly assigned U.S. Provisional Patent Application No. 61/527,387, filed on Aug. 25, 2011, by Carlson et al., titled METHOD AND APPARATUS FOR DETECTING A BIOMARKER IN THE PRESENCE OF ELECTRICAL STIMULATION, which is incorporated by reference herein in its entirety. Strategies for event detection and therapy are described in U.S. Pat. No. 7,006,872 to Gielen et al., titled, "CLOSED LOOP NEUROMODULATION FOR SUPPRESSION OF EPILEPTIC ACTIVITY," which issued on Feb. 28, 2006, which is incorporated herein by reference in its entirety.

In various embodiments, a report can be generated detailing the state of a patient's degenerative cognitive disorder. Bioelectrical information may be collected by an implanted device (e.g., an implanted device implementing the methods of any of FIGS. 1-8), transmitted externally, and displayed in a report by an external programmer or other device. Various embodiments may store event data, such as the episodes of non-motor epileptiform bioelectrical activity, a percentage of non-motor epileptiform bioelectrical activity as compared to all activity or as compared to activity that departs from baseline activity, successful abolishment of an episode of non-motor epileptiform bioelectrical activity by therapy, and/or failure of therapy to abolish an episode of non-motor epileptiform bioelectrical activity. Such data may be collected while an implanted device operates according to any embodiment, such as any of FIGS. 1-8. Metrics that can be calculated and provided as a report based on sensed data can include, but are not limited to, the number of non-motor epileptiform bioelectrical activity episodes in a period of time, the intensity of non-motor epileptiform bioelectrical activity episodes, the proportion of time in which non-motor epileptiform bioelectrical activity is present (e.g., minutes per hour), a metric indicating the efficacy of therapy in abolishing, reducing, and/or preventing non-motor epileptiform bioelectrical activity, the relative amount of improvement or worsening in the cognitive disorder, a diagnosis (e.g., mild cognitive impairment, Alzheimer's disease), number of patient seizures, and/or any other parameter or metric referenced herein, among other things.

Different frequency bands are associated with different conditions, some of which are discussed herein in various examples. Generally accepted frequency bands are shown in Table 1:

TABLE 1

| Frequency (f) Band Hertz (Hz) | Frequency Information |
| --- | --- |
| f < 4 Hz | δ (delta frequency band) |
| 4 Hz ≤ f ≤ 8 Hz | theta frequency band |
| 8 Hz ≤ f ≤ 13 Hz | α (alpha frequency band) |
| 13 Hz ≤ f ≤ 35 Hz | β (beta frequency band) |
| 35 Hz ≤ f ≤ 100 Hz | γ (gamma frequency band) |
| 100 Hz ≤ f ≤ 200 Hz | high γ (high gamma frequency band) |

It is noted that not all embodiments will perform each of the steps of the methods presented herein, and modifications to the methods are contemplated, whether by omitting, reordering, and/or adding steps. Each of the methods discussed herein can be fully or partially implemented in control circuitry of an implantable medical device (e.g., a neurostimulator configured for DBS) and/or an external device. In some embodiments, control circuitry may be configured to implement multiple of the methods described herein, such as setting discriminators for brain state detection (e.g., as described in connection with FIG. 8), discriminating between seizure and non-motor epileptiform bioelectrical activity (e.g., as described in connection with FIG. 3), establishing an association between a cognitive disorder and non-motor epileptiform bioelectrical activity in a patient (e.g., as described in connection with FIG. 4), tracking brain condition (e.g., as described in connection with FIG. 2), and/or controlling therapy delivery (e.g., as described in connection with FIGS. 1 and 5-7). As such, while each of the flowcharts and discussion might highlight different aspects and features, the techniques can be implemented in a common embodiment. The methods can also be modified in view of each other. It is also noted that not all embodiments will perform each of the steps of the methods presented herein, and modifications to the methods are contemplated, whether by omitting and/or adding steps. Each of the methods discussed herein can be fully or partially implemented in control circuitry of an implantable medical device (e.g., a neurostimulator configured for DBS) and/or an external device.

It is noted that while the flowcharts of the methods separately list sensing and therapy delivery steps, these steps may be performed at the same time and/or interspaced. In some cases, a group of pulses is delivered as part of a therapy or a test of the efficacy of pulse parameters for which a period of sensing may overlap and/or follow delivery of the group of pulses. Thus, sensing and therapy delivery may entirely, only partially, overlap. In some cases, sensing may continue uninterrupted both when therapy is being delivered and when therapy is not being delivered. Sensing may therefore be substantially continuous in some examples.

It is noted that any and all of the steps and options discussed in connection with FIGS. 1-8 and 11, or otherwise discussed herein, can be performed automatically by one or more medical devices. For example, control circuitry of an implantable medical device be configured to perform the steps of the method 100 of FIG. 1 without user intervention. Likewise, control circuitry may be configured to perform the steps of FIGS. 2-8 and 11.

Figure 9:
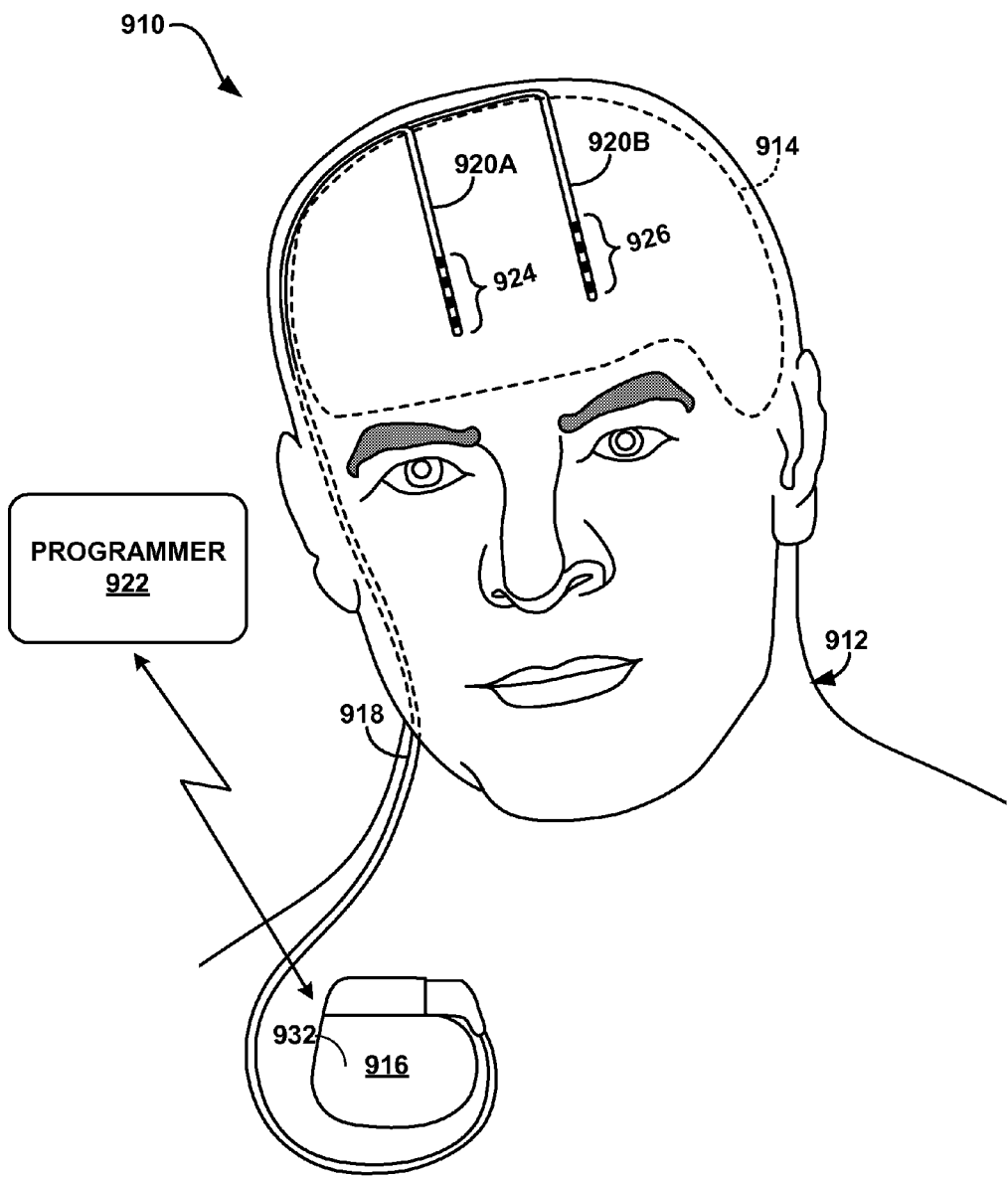
FIG. 9 is a conceptual diagram illustrating an example deep brain stimulation system for delivery of electrical stimulation to a brain of a patient.

FIG. 9 is a conceptual diagram illustrating an example therapy system 910 that delivers electrical stimulation, senses a bioelectrical response to the stimulation, monitors a brain state, and/or adjusts therapy delivery to patient 912 to manage a brain condition, among other functions described herein. System 910 includes implantable medical device (IMD) 916, lead extension 918, one or more leads 920A and 920B (collectively "leads 920") with respective sets of electrodes 924, 926 and medical device programmer 922. IMD 916 may include monitoring circuitry in electrical connection with the electrodes 924, 926 of leads 920A and 920B, respectively.

System 910 may monitor one or more bioelectrical signals of patient 912. For example, IMD 916 may include a sensing module (e.g., sensing module 944 of FIG. 10) that senses bioelectrical signals of one or more areas of brain 914. In the embodiment shown in FIG. 9, the signals may be sensed by electrodes 924, 926 and conducted to the sensing module within IMD 916 via conductors within the respective leads 920A, 920B. As described in further detail below, in some embodiments, control circuitry of IMD 916 or another device (e.g., programmer 922) monitors the bioelectrical signals within brain 914 of patient 912 to identify one or more biomarkers and determine a patient state, such as a seizure state, an episode of non-motor epileptiform bioelectrical activity, a normal (baseline) patient state, an episode of excessive hippocampal bioelectrical activity and/or perform the other functions referenced herein including those referenced in connection with FIGS. 1-8 and 11. Control circuitry of IMD 916 or another device (e.g., programmer 922) may analyze bioelectrical signals and/or other signals, detect non-motor epileptiform bioelectrical activity, and/or patient states, and/or control delivery of therapy to brain 914 in a manner that treats a brain condition of patient 912.

In some examples, the sensing module of IMD 916 may receive the bioelectrical signals from electrodes 924, 926 or other electrodes positioned to monitor bioelectrical signals of patient 912 (e.g., if housing 932 of IMD 916 is implanted in or proximate brain 914, an electrode of housing 932 can be used to sense bioelectrical signals and/or deliver stimulation to brain 914). Electrodes 924, 926 may also be used to deliver electrical stimulation from stimulation generator 942 to target sites within brain 914 as well as to sense bioelectrical signals within brain 914. However, IMD 916 can also use separate sensing electrodes to sense the bioelectrical signals. In some embodiments, the sensing module of IMD 916 may sense bioelectrical signals via one or more of the electrodes 924, 926 that are also used to deliver electrical stimulation to brain 914. In other embodiments, one or more of electrodes 924, 926 may be used to sense bioelectrical signals while one or more different electrodes 924, 926 may be used to deliver electrical stimulation.

Examples of the monitored bioelectrical signals include, but are not limited to, an EEG signal, an ECoG signal, an MEG (magnetoencephalography) signal, and/or a LFP signal sensed from within or about one or more locations of brain 914. These and other signals can be used to perform various functions referenced herein.

As described in further detail below, IMD 916 may deliver therapy to any suitable portion of brain 914. For example, system 910 may provide therapy to correct a brain disorder and/or manage symptoms of a degenerative brain condition. Patient 912 ordinarily will be a human patient. In some cases, however, system 910 may be applied to other mammalian or non-mammalian non-human patients.

IMD 916 may include a module that includes a stimulation generator 942 that generates and delivers electrical stimulation therapy to one or more regions of brain 914 of patient 912 via the electrodes 924, 926 of leads 920A and 920B, respectively. In the example shown in FIG. 9, system 910 may be referred to as deep brain stimulation system because IMD 916 may provide electrical stimulation therapy directly to tissue within brain 914, e.g., a tissue site under the dura mater of brain 914. In some other embodiments, leads 920 may be positioned to sense brain activity and/or deliver therapy to a surface of brain 914, such as the cortical surface of brain 914, or other location in or along the patient 912.

In the example shown in FIG. 9, IMD 916 may be implanted within a subcutaneous pocket below the clavicle of patient 912. In other embodiments, IMD 916 may be implanted within other regions of patient 912, such as a subcutaneous pocket in the abdomen or buttocks of patient 912 or proximate the cranium of patient 912. Implanted lead extension 918 is coupled to IMD 916 via a connector block (also referred to as a header), which may include, for example, electrical contacts that electrically couple to respective electrical contacts on lead extension 918. The electrical contacts electrically couple the electrodes 924, 926 carried by leads 920 to IMD 916. Lead extension 918 traverses from the implant site of IMD 916 within a chest cavity of patient 912, along the neck of patient 912 and through the cranium of patient 912 to access brain 914. Generally, IMD 916 is constructed of a biocompatible material that resists corrosion and degradation from bodily fluids. IMD 916 may comprise a hermetic housing 932 to substantially enclose control circuitry components, such as a processor, sensing module, therapy module, and memory. In some implementations, IMD 916 and other components (e.g., leads 920) may be implanted only in the head of the patient (e.g., under the scalp) and not in the chest and neck regions.

Electrical stimulation may be delivered to one or more areas of brain 914, which may be selected based on many factors, such as the type of patient condition for which system 910 is implemented to manage. In some cases, leads 920 may be implanted within the right and left hemispheres of brain 914 (e.g., as illustrated in FIG. 9) while, in other examples, one or both of leads 920 may be implanted within one of the right or left hemispheres. Other implant sites for leads 920 and IMD 916 are contemplated. For example, in some examples, IMD 916 may be implanted on or within cranium. In addition, in some examples, leads 920 may be coupled to a single lead that is implanted within one hemisphere of brain 914 or implanted through both right and left hemispheres of brain 914.

Leads 920 may be positioned to deliver electrical stimulation to one or more target tissue sites within brain 914 to manage patient symptoms associated with a disorder of patient 912. Tissue targeted for stimulation may be the same tissue that is monitored for non-motor epileptiform bioelectrical activity. However, in some cases the tissue targeted for stimulation will be different from the tissue which generates the non-motor epileptiform bioelectrical activity being monitored. Leads 920 may be implanted to position electrodes 924, 926 at desired locations of brain 914 through respective holes in cranium. Leads 920 may be placed at any location(s) within or along brain 914 such that electrodes 924, 926 are capable of providing electrical stimulation to target tissue sites of brain 914 during treatment and/or proximate tissue being monitored. In some embodiments, leads may be placed such that electrodes 924, 926 directly contact or are proximate tissue targeted for stimulation and/or monitoring.

In the example shown in FIG. 9, electrodes 924, 926 of leads 920 are shown as ring electrodes. Ring electrodes are typically capable of sensing and/or delivering an electrical field to any tissue adjacent to leads 920 (e.g., in all directions away from an outer perimeter of leads 920). In other examples, electrodes 924, 926 of leads 920 may have different configurations. For example, electrodes 924, 926 of leads 920 may have a complex electrode array geometry that is capable of producing shaped electrical fields. The complex electrode array geometry may include multiple electrodes (e.g., partial ring or segmented electrodes) around the perimeter of each lead 920, rather than a ring electrode. In this manner, electrical brain sensing and/or electrical stimulation may be associated with a specific direction from leads 920 (e.g., less than the entire outer perimeter of leads 920) to enhance direction sensing and/or therapy efficacy and reduce possible adverse side effects from stimulating a large volume of tissue in the case of stimulation. As such, electrodes can be positioned to preferentially sense from one side of a lead and to stimulate targeted tissue and avoid stimulating non-targeted tissue. In examples, leads 920 may have shapes other than elongated cylinders as shown in FIG. 9. For example, leads 920 may be paddle leads, spherical leads, bendable leads, or any other type of shape effective in treating patient 912.

In some embodiments, outer housing 932 of IMD 916 may include one or more stimulation and/or sensing electrodes. For example, housing 932 can comprise an electrically conductive material that is exposed to tissue of patient 912 (e.g., the can containing circuitry being electrical connected to sensing and/or stimulation circuitry) when IMD 916 is implanted in patient 912, or an electrode can be attached to housing 932.

In some examples, the location of the electrodes 924, 926 within brain 914 can be determined based on analysis of a bioelectrical signal of the patient sensed via one or more of the electrodes 924, 926. For example, a particular physiological structure (e.g., the amygdala) may exhibit a unique electrical signal and, thus, facilitate positioning of the electrodes of the lead at the desired implant location through monitoring of the bioelectrical signal.

Leads 920 may be implanted within a desired location of brain 914 via any suitable technique, such as through respective burr holes in a skull of patient 912 or through a common burr hole in the cranium. Leads 920 may be placed at any location within brain 914 such that electrodes 924, 926 of leads 920 are capable of sensing electrical activity of the brain areas and/or providing electrical stimulation to targeted tissue for treatment.

In some embodiments, a processor of system 910 (e.g., a processor of programmer 922 or IMD 916) controls delivery of electrical stimulation by activating electrical stimulation, deactivating electrical stimulation, increasing the intensity of electrical stimulation, or decreasing the intensity of electrical stimulation delivered to brain 914 to titrate electrical stimulation therapy. In this way, therapy can be started, stopped, and/or changed by a processor in any manner and based on any parameter or finding as discussed herein.

System 910 may also store a plurality of stimulation programs (e.g., a set of electrical stimulation parameter values). A processor of IMD 916 or programmer 922 may select a stored stimulation program that defines electrical stimulation parameter values for delivery of electrical stimulation to brain 914 based on a characterization of neural activation. Where IMD 916 delivers electrical stimulation in the form of electrical pulses, for example, the stimulation therapy may be characterized by selected pulse parameters, such as pulse amplitude, pulse rate, and pulse width. In addition, if different electrodes are available for delivery of stimulation, the therapy may be further characterized by different electrode combinations, which can include selected electrodes and their respective polarities. The therapy may be characterized by stimulation delivery settings based on a patient response profile, such as using stimulation parameters shown to reduce non-motor epileptiform bioelectrical activity or otherwise determined by the embodiments referenced herein (e.g., as discussed in connection with FIGS. 1-8).

External programmer 922 wirelessly communicates with IMD 916 as needed to provide or retrieve information. For example, external programmer 922 may receive sensed data and/or information from IMD 916, as well as send therapy program information to IMD 916. Programmer 922 is an external computing device that the user, e.g., the clinician and/or patient 912, may use to communicate with IMD 916. For example, programmer 922 may be a clinician programmer that the clinician uses to communicate with IMD 916 and program one or more therapy programs for IMD 916. Additionally or alternatively, programmer 922 may be a patient programmer that allows patient 912 to input information (e.g., a self-evaluated assessment regarding symptoms and/or patient state), select programs, and/or view and modify therapy parameters. In some embodiments, a programmer 922 can display information about an assessment of a cognitive disorder, a log of detected events, and/or any other information referenced herein.

Programmer 922 is a medical device that may be a handheld computing device with a display viewable by the user and an interface for providing input to programmer 922 (i.e., a user input mechanism) and/or displaying information received from the IMD 916. For example, programmer 922 may include a small display screen (e.g., a liquid crystal display (LCD) or a light emitting diode (LED) display) that presents information to the user. In addition, programmer 922 may include a touch screen display, keypad, buttons, a peripheral pointing device or another input mechanism that allows the user to navigate through the user interface of programmer 922 and provide input. A screen (not shown) of programmer 922 may be a touch screen that allows the user to provide input directly to the user interface shown on the display. The user may use a stylus or finger to provide input to the display, such as an indication that the patient is in a particular patient state as part of a training phase as discussed herein.

In various embodiments, programmer 922 as a medical device may be a larger workstation or a separate application within another multi-function device, rather than a dedicated computing device. For example, the multi-function device may be a notebook computer, tablet computer, workstation, cellular phone, personal digital assistant or another computing device. The circuitry components of a programmer and/or other external device(s), such as equivalent circuitry to that of FIG. 10, can be control circuitry as means for performing functions as described herein (e.g., assessing a cognitive disorder based on non-motor epileptiform bioelectrical activity and in some cases further controlling a therapy based on the assessment), including those described in association with FIGS. 1-8. Various embodiments of external circuitry may include a screen on which information can be presented. The output of a screen may be controlled by control circuitry.

When programmer 922 is configured for use by the clinician, programmer 922 may be used to transmit initial programming information to IMD 916. This initial information may include hardware information, such as the type of leads 920, the arrangement of electrodes 924, 926 on leads 920, the position of leads 920 within brain 914, initial programs defining therapy parameter values, and any other information that may be useful for programming into IMD 916. Programmer 922 may also be capable of controlling circuitry of the IMD 916 in carrying out the functions described herein.

The clinician may also store therapy programs within IMD 916 with the aid of programmer 922. During a programming session, the clinician may determine one or more stimulation programs that may effectively bring about a therapeutic outcome that treats a brain condition, such with as the therapy parameter setting techniques of FIGS. 3-5. During the programming session, the clinician may evaluate the efficacy of the one or more stimulation settings (e.g., pulse amplitude, pulse width, pulse frequency, and a resultant bioelectrical response) based on one or more findings of a sensed signal (e.g., based on whether the stimulation is abolishing non-motor epileptiform bioelectrical activity). In some examples, programmer 922 may assist the clinician in the creation/identification of stimulation programs by providing a methodical system for identifying potentially effective stimulation parameter values, such as by recommending stimulation parameters and/or electrode(s). In some examples, the processor of programmer 922 may calculate and display one or more therapy metrics for evaluating and comparing therapy programs available for delivery of therapy from IMD 916 to patient.

Programmer 922 may also provide an indication to patient 912 when therapy is being delivered which may aid the assessment of therapy efficacy. For example, concurrent with or following the delivery of electrical stimulation, the patient may evaluate whether he or she seems to have symptoms (e.g., of a cognitive difficulty) by answering questions presented on the programmer 922 corresponding to times when baseline bioelectrical activity levels are sensed, when non-motor epileptiform bioelectrical activity is detected, and/or during a washout period. The information may be used to determine the relationship between stimulation intensity and a bioelectrical response, such as in the training phase of FIG. 8.

Whether programmer 922 is configured for clinician or patient use, programmer 922 may be configured to communicate with IMD 916 and, optionally, another computing device, via wireless communication. Programmer 922, for example, may communicate via wireless communication with IMD 916 using radio frequency (RF) telemetry techniques known in the art. Programmer 922 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. Programmer 922 may also communicate with other programming or computing devices via exchange of removable media, such as magnetic or optical disks, memory cards or memory sticks. Further, programmer 922 may communicate with IMD 916 and another programmer via remote telemetry techniques known in the art, communicating via a local area network (LAN), wide area network (WAN), public switched telephone network (PSTN), or cellular telephone network, for example.

Figure 10:
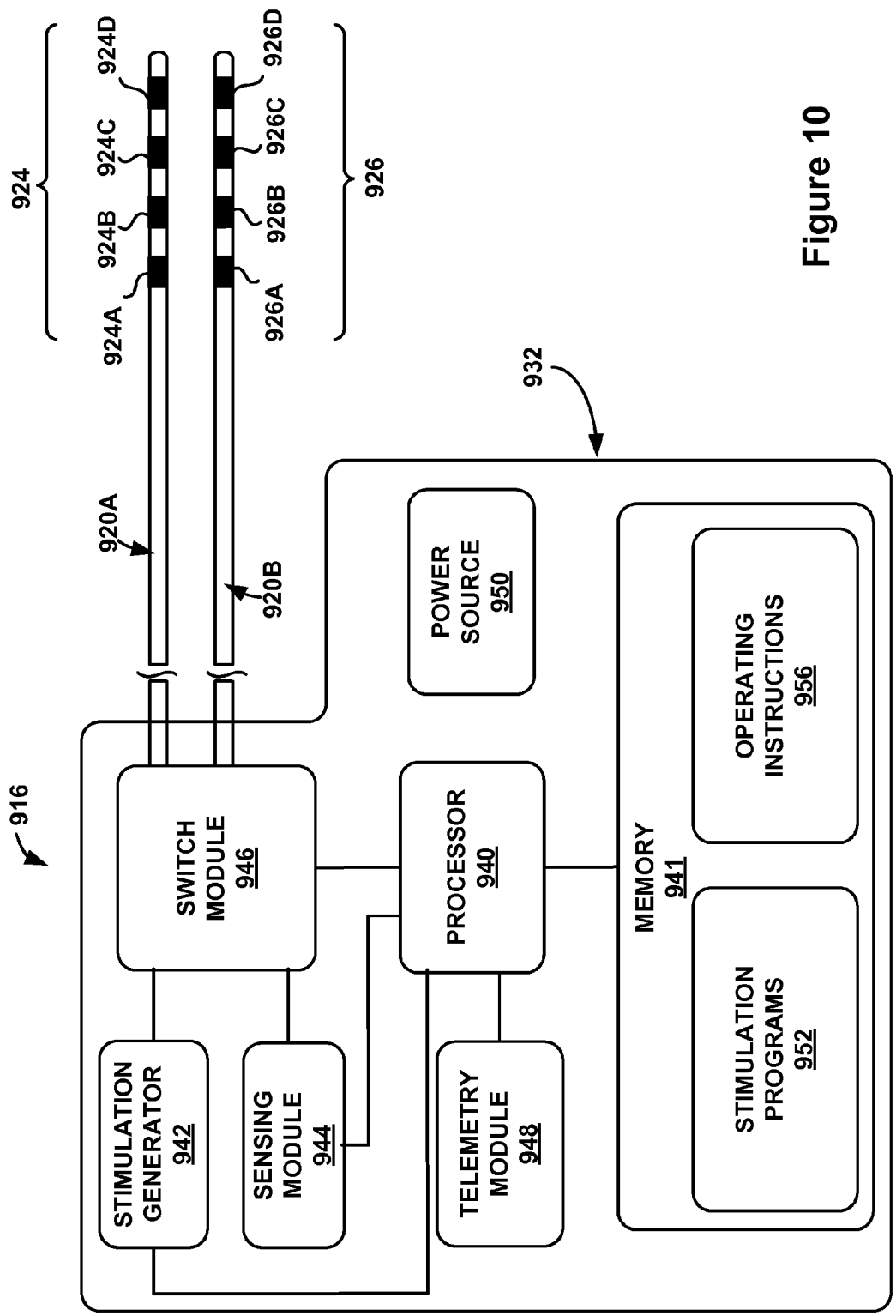
FIG. 10 is a conceptual diagram illustrating an example therapy system for delivery of electrical stimulation to a brain of a patient.

FIG. 10 is a functional block diagram illustrating components of IMD 916. In the configuration shown in FIG. 10, IMD 916 includes processor 940, memory 941, stimulation generator 942, and sensing module 944, which can be control circuitry as means for performing functions as described herein (e.g., detecting non-motor epileptiform bioelectrical activity, assessing a cognitive disorder based on the non-motor epileptiform bioelectrical activity, controlling a therapy based on the assessment, and/or any of the techniques referenced in connection with FIG. 1-8). Memory 941 may include any volatile or non-volatile media, such as a random access memory (RAM), read only memory (ROM), non-volatile RAM (NVRAM), electrically erasable programmable ROM (EEPROM), flash memory, and the like. Memory 941 may store computer-readable instructions that, when executed by processor 940, cause IMD 916 to perform various functions described herein. Memory 941 may include operating instructions 956 executable by the processor 940 for causing the IMD 916 to carry out the various functions referenced herein, including those discussed in association with FIGS. 1-8. Memory 941 may store therapy instructions as part of stimulation programs 952 that are available to be selected by processor 940 in response to particular conditions (e.g., an episode of non-motor epileptiform bioelectrical activity) detected by the sensing module 944 or determination of a particular patient state. In addition, processor 940 may be configured to record diagnostic information, such as sensed signals, measured values, detected events, biomarker signatures, patient state episode information, and the like in memory 941 or another memory or storage device. The various functions and techniques described herein may be performable automatically by the IMD 916 by processor 940 execution of operating instructions 956 and stimulation programs 952 stored in memory 941.

The steps, procedures, techniques, etc. referenced herein may be carried out in part by, for example, software instructions, such as those used to define a software or computer program. The non-transitory computer-readable medium (e.g., memory 941) may store instructions (e.g., operating instructions 956 and stimulation programs 952) executable by a processor (e.g., processor 940 and/or of an external device) to carry out the steps, procedures, techniques, etc. In this way, control circuitry can be configured to perform the various steps, procedures, techniques, etc. as described herein, including those discussed in association with FIGS. 1-8. The computer-readable medium may be a computer-readable storage medium such as a storage device (e.g., a disk drive, or an optical drive), memory (e.g., a Flash memory, random access memory or RAM) or any other type of volatile or non-volatile memory that stores processor executable instructions (e.g., in the form of a computer program or other executable) as part of control circuitry to carry out the functions described herein.

Processor 940 may be configured to cause stimulation generator 942 to deliver electrical stimulation with pulse voltage or current amplitudes, pulse widths, and frequencies (i.e., pulse rates) as part of control circuitry, and electrode combinations specified by the stimulation programs 952, e.g., as stored in memory 941. Processor 940 may control stimulation generator 942 to deliver each pulse, or a group of pulses, according to a different program of the stimulation programs, such that multiple programs of stimulation are delivered on an interleaved or alternating basis, e.g., having different delays or responding to different biomarkers, bioelectrical responses, or patient states. In some embodiments, processor 940 may control stimulation generator 942 to deliver a substantially continuous stimulation waveform rather than pulsed stimulation.

As shown, the set of electrodes 924 of lead 920A includes electrodes 924A, 924B, 924C, and 924D, and the set of electrodes 926 of lead 920B includes electrodes 926A, 926B, 926C, and 926D. Processor 940 may control switch module 946 to route sensed signals to sensing module 944 and/or apply the stimulation signals generated by stimulation generator 942 to selected combinations of electrodes 924, 926. In particular, switch module 946 may couple stimulation signals to selected conductors within leads 920, which, in turn, deliver the stimulation signals across selected electrodes 924, 926. Switch module 946 may be a switch array, switch matrix, multiplexer, or any other type of switching module configured to selectively couple stimulation energy to selected electrodes 924, 926 and to selectively sense bioelectrical signals with selected electrodes 924, 926. Hence, stimulation generator 942 is coupled to electrodes 924, 926 via switch module 946 and conductors within leads 920. In some embodiments, however, IMD 916 does not include switch module 946.

Sensing module 944 is configured to sense bioelectrical signals of patient 912 via a selected subset of electrodes 924, 926, or with one or more electrodes 924, 926 and at least a portion of a conductive outer housing 932 of IMD 916, an electrode on an outer housing of IMD 916, or another reference. In some embodiments, sensing module 944 may measure the amplitude of a signal and relate the value to processor 940. Processor 940 may control switch module 946 to electrically connect sensing module 944 to selected electrodes 924, 926. In this way, sensing module 944 may selectively sense bioelectrical signals with different combinations of electrodes 924, 926 (and/or a reference other than an electrode 924, 926). Although the electrodes 924, 926 are principally described as being implanted within a brain in the manner of DBS, other locations are additionally or alternatively contemplated. For example, electrodes may be deployed at selected tissue sites or on selected surfaces of a human patient, such as on the brain, along the cortex, proximate the spinal cord, on the scalp, or elsewhere. As an example, scalp electrodes may be used to measure or record EEG signals. As another example, electrodes implanted at the surface of the cortex may be used to measure or record ECoG signals. In some embodiments, an external device may be worn with sensing elements positioned at a desired location adjacent the patient to detect a bioelectrical signal.

Sensing module 944 may form part of a sensor circuit configured to monitor a variety of signals via a variety of different sensing elements, such as a bioelectrical signal via electrodes 924, 926, and/or other physiological signals. Sensing module 944 may include amplifiers, filters, modulators, and other circuitry for conditioning and measuring one or more parameters of signals. Sensing module 944 and/or processor 940 (and/or other circuitry) may condition one or more sensed signals to account for noise and/or identify a bioelectrical response according to any technique referenced herein. In some embodiments, sensing module 944 may directly process signals obtained from electrodes 924, 926 or other sensing elements with little or no preprocessing by other components. In other embodiments, sensing module 944 may include preprocessing circuitry to process or convert signals for analysis by processor 940 or other circuitry. In some embodiments, sensing module 944 includes circuitry configured to measure one or more parameters of an electrical signal, such as amplitude, and processor 940 receives an output from the telemetry module 948 of an indication of the measurement for further analysis as discussed herein, such as extracting spectral characteristics of the signal. Such circuitry may further discriminate which one of a plurality of different states, including detecting a non-motor epileptiform bioelectrical activity episode.

A sensing module 944 that includes a circuit architecture that directly extracts energy in key frequency bands of a bioelectrical brain signal may be useful for tracking the power fluctuations within the selected frequency bands and detecting a non-motor epileptiform bioelectrical activity episode based on the bioelectrical brain signal. In some examples, the energy in particular frequency band or bands of a bioelectrical signal may be used as a parameter that serves as a feature value in a supervised learning algorithm, such as an support vector algorithm or an support vector machine-based classification algorithm generated based on the support vector machine algorithm.

Stimulation generator 942, under the control of processor 940, generates stimulation signals for delivery to patient 912 via selected combinations of electrodes 924, 926. Processor 940 controls stimulation generator 942 according to stimulation programs 952 stored in memory 941 to apply particular stimulation parameter values specified by one or more programs, such as amplitude, pulse width, timing, and pulse rate. The stimulation programs 952 may also specify the timing of stimulation, such as the timing of stimulation according to a cycled stimulation regimen. In various embodiments, stimulation generator 942 generates and delivers stimulation signals to one or more target portions of brain 914 via a select combination of electrodes 924, 926.

Although sensing module 944 is incorporated into a common housing 932 with stimulation generator 942 and processor 940, in other examples, sensing module 944 is in a physically separate outer housing from outer housing 932 of IMD 916 and communicates with processor 940 via wired or wireless communication techniques.

One or more electrodes can be placed proximate a target site for sensing bioelectrical activity generated from tissue of the target site and/or delivering electrical stimulation to the tissue of the target site. A target for sensing and/or stimulation for addressing a neurological condition can be in, but are not limited to, the hippocampus. The hippocampal region (dentate gyms, hippocampus proper and subicular complex) can also be targeted. Another target is the entorhinal cortex, which plays a role in memory formation. Further targets can include the entorhinal, perirhinal, and parahippocampal cortices. Targets can include the formix, anterior nucleus, and the thalamus. Other targets include, but are not limited to, the cortex, including, but not limited to, the temporal cortex, occipital cortex, parietal cortex, and frontal cortex. In some cases, any structure within the limbic system can be targeted. Targets for sensing and/or stimulation may not be limited to particular areas, but rather may be directed to functionally connected circuits of the brain, such as along the Circuit of Papez. The Circuit of Papez is one of the major pathways of the limbic system, and the regions of brain within the Circuit of Papez includes the anterior nucleus, internal capsule, cingulate, hippocampus, formix, entorhinal cortex, mammillary bodies, and mammillothalamic tract. The areas of the brain within the Circuit of Papez may be considered to be functionally connected, such that activity within one part of the Circuit of Papez may affect activity within another part of the Circuit of Papez. In this way, the delivery of stimulation to one area (e.g., the anterior nucleus) of the Circuit of Papez may affect the brain activity level within another area of the Circuit of Papez (e.g., the hippocampus). As such, direct and indirect stimulation of various brain structures is contemplated herein.

The site targeted for therapy delivery may be the same brain area as the sense location, such as the hippocampus. However, in various embodiments, the sense location and target site for stimulation are different areas of the brain that are networked.

Multiple different disease conditions could potentially benefit from a therapy as described herein. The embodiments referenced herein may be applicable to any brain stimulation therapy to reduce or otherwise change some aspect of bioelectrical activity such as non-motor epileptiform bioelectrical activity or otherwise excessive bioelectrical activity. Various embodiments referenced herein could be used to reduce symptoms of Alzheimer's disease and/or mild cognitive impairment or improve the memory and/or concentration functions of a patient suffering from a neurological condition. Embodiments of this disclosure could be used to treat symptoms of disorders including without limitation depression, schizophrenia, addiction, sleep dysfunction, obsessive compulsive disorder, post-traumatic stress disorder, panic disorder, autism, sleep disorders, Tourette's syndrome, and obesity.

While the main example embodiments used herein to describe various features and options of the present disclosure concern delivering stimulation therapy, various other embodiments can additionally or alternatively deliver one or more drugs to the patient to address the cognitive disorder. For example, IMD 916 may deliver a therapeutic agent to the patient to manage the cognitive disorder. Therapy delivery may be started, stopped, increased in intensity, decreased in intensity, or otherwise titrated in any other way as described herein. In such examples, IMD 916 may include a fluid pump or another device that delivers a therapeutic agent in some metered or other desired flow dosage to the therapy site within the patient from a reservoir within IMD 916 via a catheter. IMD 916 may deliver the therapeutic agent upon assessing the cognitive disorder based on non-motor epileptiform bioelectrical activity. The catheter used to deliver the therapeutic agent to the patient may include one or more electrodes for sensing bioelectrical brain signals of the patient.

Examples of therapeutic agents that IMD 916 may deliver to the patient include, but are not limited to, lorazepam, carbamazepine, oxcarbazepine, valproate, divalproex sodium, acetazolamide, diazepam, phenytoin, phenytoin sodium, felbamate, tiagabine, levetiracetam, clonazepam, lamotrigine, primidone, gabapentin, phenobarbital, topiramate, clorazepate, ethosuximide, and zonisamide. Other therapeutic agents may also provide effective therapy to manage the patient's cognitive disorder, e.g., by minimizing the severity, duration, and/or frequency of the patient's non-motor epileptiform bioelectrical activity episodes. In other examples, IMD 916 may deliver a therapeutic agent to tissue sites within the patient other than the brain.

Telemetry module 948 supports wireless communication between IMD 916 and an external programmer 922 or another computing device under the control of processor 940. Processor 940 of IMD 916 may receive, as updates to sensing and/or stimulation programs, information concerning the therapy programs, thresholds, and/or values for stimulation parameters for delivering therapy from programmer 922 via telemetry module 948. The updates to the stimulation, sensing, or other programs may be stored within stimulation programs 952 or other section of memory 941. Telemetry module 948 in IMD 916, as well as telemetry modules in other devices and systems described herein, such as programmer 922, may accomplish communication by RF communication and/or inductance techniques, among other transcutaneous communication techniques. For example, telemetry module 948 may communicate with external medical device programmer 922 via proximal inductive interaction of IMD 916 with programmer 922. Accordingly, telemetry module 948 may send information to external programmer 922 on a continuous basis, at periodic intervals, or upon request from IMD 916 or programmer 922. For example, processor 940 may transmit sensed signals, biomarker identification information, episodic information, stimulation history information, and/or information concerning patient states (e.g., baseline, seizure, and/or non-motor epileptiform bioelectrical activity states) to programmer 922 via telemetry module 948.

Power source 950 delivers operating power to various components of IMD 916. Power source 950 may include a small rechargeable or non-rechargeable battery and a power generation circuit to produce the operating power. Recharging may be accomplished through proximal inductive interaction between an external charger and an inductive charging coil within IMD 916. In various embodiments, traditional batteries may be used.

The techniques described in this disclosure, including those attributed to programmer 922, IMD 916, processor, control circuitry or various constituent components, may be implemented, at least in part, in hardware, software, firmware or any combination thereof. Such hardware, software, firmware may be implemented within the same device or within separate devices to support the various operations and functions described in this disclosure. While the techniques described herein are primarily described as being performed by processor 940 of IMD 916 and/or processor of a programmer or other external device as part of control circuitry, any of the one or more parts of the techniques described herein may be implemented by a processor of one of IMD 916, programmer 922, or another computing device, alone or in combination with each other, as control circuitry. For example, the various functional options discussed in connection with FIGS. 1-8 and elsewhere herein can be implemented by a processor (e.g., processor 940) executing program instruction stored in memory (e.g., memory 941), as control circuitry, that performs the various described functions.

Although the control circuitry of FIG. 10 is generally illustrated and described in terms of an implantable medical device, the control circuitry could alternatively be embodied in an at least partially external device and, depending on the therapy and/or circuitry configuration, may be wholly external.

The techniques described in this disclosure, including those discussed in connection with FIGS. 1-8 and 11 and those attributed to programmer, IMD, processor, and/or control circuitry, or various constituent components, may be implemented wholly or at least in part, in hardware, software, firmware or any combination thereof. A processor, as used herein, refers to any number and/or combination of a microprocessor, a digital signal processor (DSP), an application specific integrated circuit (ASIC), a field-programmable gate array (FPGA), microcontroller, processing chip, gate arrays, and/or any other equivalent integrated or discrete logic circuitry. "Control circuitry" as used herein refers to at least one of the foregoing logic circuitry as a processor, alone or in combination with other circuitry, such as memory or other physical medium for storing instructions, as needed to carry about specified functions (e.g., a processor and memory having stored program instructions executable by the processor as control circuitry configured to carry out one or more specified functions, such as sensing one or more bioelectrical brain signals, detecting non-motor epileptiform bioelectrical activity, assessing a brain condition based on the non-motor epileptiform bioelectrical activity, and controlling a therapy based on the assessment). The functions referenced herein (e.g., those discussed in connection with FIGS. 1-8 and 11) may be embodied as firmware, hardware, software or any combination thereof as part of control circuitry specifically configured (e.g., with programming) to carry out those functions, such as in means for performing the functions referenced herein. The steps described herein may be performed by a single processing component or multiple processing components, the latter of which may be distributed amongst different coordinating devices (e.g., an IMD and an external programmer). In this way, control circuitry may be distributed between multiple devices, including an implantable medical device and an external medical device in various systems. In addition, any of the described units, modules, or components may be implemented together or separately as discrete but interoperable logic devices of control circuitry. Depiction of different features as modules or units is intended to highlight different functional aspects and does not necessarily imply that such modules or units must be realized by separate hardware or software components and/or by a single device. Rather, functionality associated with one or more module or units, as part of control circuitry, may be performed by separate hardware or software components, or integrated within common or separate hardware or software components of the control circuitry.

When implemented in software, the functionality ascribed to the systems, devices and control circuitry described in this disclosure may be embodied as instructions on a physically embodied computer-readable medium such as RAM, ROM, NVRAM, EEPROM, FLASH memory, magnetic data storage media, optical data storage media, or the like, the medium being physically embodied in that it is not a carrier wave, as part of control circuitry. The instructions may be executed to support one or more aspects of the functionality described in this disclosure.

While the detection of non-motor epileptiform bioelectrical activity is principally described herein, some embodiments may concern the detection of excessive hippocampal bioelectrical activity associated with a cognitive disorder and controlling a therapy based on the excessive hippocampal bioelectrical activity. Episodes of excessive hippocampal bioelectrical activity may result in damage to the brain (e.g., including but not necessarily limited to the hippocampus), whether by the episodes directly damaging the brain, the damage occurring as a result of the brain network's response to the episodes, or some other mechanism. The damage may accelerate the decline of brain function as part of a degenerative cognitive disorder.

Such excessive hippocampal bioelectrical activity may not necessarily resemble epileptiform bioelectrical activity. In either case, excessive hippocampal bioelectrical activity can be detected based on a measure of bioelectrical activity (e.g., RMS or spectral energy in a particular frequency range) sensed from the hippocampus exceeding a threshold or some other mark. Excessive hippocampal bioelectrical activity can be detected based on the measure of bioelectrical activity deviating from a baseline previously set for the patient, such as deviating a predetermined amount (e.g., 50%) above a baseline of hippocampal bioelectrical activity for a predetermined amount of time (e.g., 5 seconds). The establishment of a baseline level of bioelectrical activity for a patient is discussed herein.

Episodes of excessive bioelectrical activity, such as bioelectrical activity of the hippocampus or hippocampal region, can be associated with a worsening cognitive disorder. An increasing number of episodes, an increasing rate of episode occurrence, increasing intensity (e.g., even higher levels of activity), and/or an increasing relative amount of time episodes are occurring, among other metrics of excessive bioelectrical activity, can each indicate a worsening cognitive condition. Therapy can accordingly be titrated based on the cognitive condition, such as starting or increasing therapy intensity based on a worsening cognitive condition or stopping or decreasing therapy intensity based on an improving cognitive condition as indicated by increasing or decreasing measures of excessive bioelectrical activity.

Figure 11:
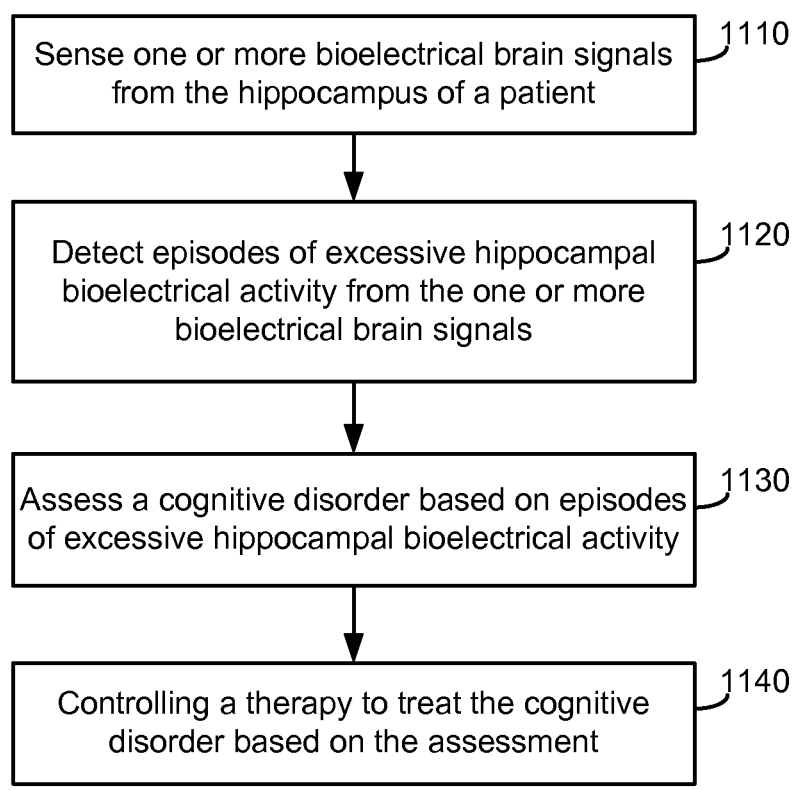
FIG. 11 is a flowchart for assessing a cognitive disorder and further controlling a therapy based on episodes of excessive hippocampal bioelectrical activity.

FIG. 11 illustrates a flowchart of a method 1100 for assessing a cognitive disorder and further controlling a therapy based on episodes of excessive hippocampal bioelectrical activity. The method 1100 includes sensing 1110 one or more bioelectrical brain signals from a hippocampus of a patient. Sensing 1110 can include receiving one or more bioelectrical signals (e.g., a LFP signal) into sensing circuitry through an electrode within or proximate the hippocampus. Sensing 1110 may be performed in any manner referenced herein, and may be performed by sensing circuitry as referenced herein.

The method 1100 further includes detecting 1120 excessive hippocampal bioelectrical activity from the sensed 1110 bioelectrical brain signals. Detection 1120 of excessive hippocampal bioelectrical activity may be done in any manner referenced herein, such as by detecting an increase in spectral energy, RMS value, or any other metric of the amplitude and/or energy of the signal. For example, the amplitude of an LFP signal sensed via an electrode in direct contact with the hippocampus of a patient exceeding a threshold for a predetermined amount of time may be the basis for recognizing an episode of excessive hippocampal bioelectrical activity. Detection 1120 may be facilitated by the techniques discussed in connection with FIG. 8, where an algorithm is generated for detecting excessive hippocampal bioelectrical activity instead of, or in addition to, detecting non-motor epileptiform bioelectrical activity.

The method 1100 further includes assessing 1130 a cognitive disorder based on the detected 1120 excessive hippocampal bioelectrical activity. Assessing 1130 the cognitive disorder can include determining the number of excessive hippocampal bioelectrical activity episodes over a time period, determining a percentage of excessive hippocampal bioelectrical activity as compared to all activity that departs from baseline activity or to a certain type of activity that departs from baseline activity, determining the rate of occurrence of excessive hippocampal bioelectrical activity episodes, determining the intensity of the excessive hippocampal bioelectrical activity, and/or determining the trend of the excessive hippocampal bioelectrical activity, among other statistical techniques for assessing the level of excessive hippocampal bioelectrical activity. The statistical techniques can be used to determine the relative level of excessive hippocampal bioelectrical activity that is occurring. In some cases, the statistical metrics can be compared to a scale (e.g., a ten point scale covering severity levels of the cognitive disorder), a threshold (e.g., representing the presence or absence of a particular cognitive disorder), population data (e.g., representing the prevalence of excessive hippocampal bioelectrical activity in healthy individuals or individuals having a particular cognitive disorder), past data for the same patient (e.g., previously collected), and/or other data to characterize the patient's cognitive disorder. The assessment 1130 can include determining whether a cognitive disorder is present or absent, such as by diagnosing a patient as having a particular cognitive disorder based on the prevalence of excessive hippocampal bioelectrical activity episodes (e.g., whether the number of episodes, rate of occurrence, or another measure of the prevalence of episodes crosses a threshold). The assessment may be used to track the cognitive disorder and provide an output in some embodiments. Such an output may comprise a report printed out and/or displayed on a screen of a computing device such as a programmer and/or controlling 1140 a therapy.

Some embodiments of the method 1100 may further include controlling 1140 delivery of a therapy to treat the cognitive disorder. The delivery of the therapy may be controlled 1140 based on the assessment 1130 of the cognitive disorder in any manner discussed herein for controlling a therapy, including starting, stopping, increasing, and/or decreasing therapy delivery. The therapy may comprise any therapy referenced herein, including a drug therapy and/or a DBS therapy. In various cases, the therapy can reduce the bioelectrical activity level within the hippocampus to help mitigate symptoms of the excessive hippocampal bioelectrical activity, such as by lowering the likelihood of occurrence, duration, and/or frequency of episodes of excessive hippocampal bioelectrical activity and minimizing the damage from the episodes or from the brain's response to the episodes.

Various embodiments in accordance with FIG. 11 or other embodiments for assessing a cognitive condition and controlling a therapy based on excessive hippocampal bioelectrical activity can employ any of the techniques referenced herein. For example, control circuitry (e.g., as in FIG. 10) of a system (e.g., of FIG. 9) may be configured to implement the method 1100 of FIG. 11, which may be in addition to setting discriminators for brain state detection based on excessive hippocampal bioelectrical activity (e.g., in a manner similar to FIG. 8), discriminating between excessive hippocampal bioelectrical activity and a seizure or a different event (e.g., in a manner similar to FIG. 3), establishing an association between a cognitive disorder and excessive hippocampal bioelectrical activity in a patient based on cognitive performance (e.g., in a manner similar to FIG. 4), tracking brain condition based on excessive hippocampal bioelectrical activity (e.g., in a manner similar to FIG. 2), and/or controlling therapy delivery (e.g., in a manner similar to one or more of FIGS. 1 and/or 5-7). As such, the embodiments of FIGS. 2-10 could be redirected to excessive hippocampal bioelectrical activity instead of non-motor epileptiform bioelectrical activity.

While the embodiment of FIG. 11 is described in term of reducing excessive hippocampal bioelectrical activity, this method and options are application to sensing 1110 bioelectrical signals, detecting 1120 excessive bioelectrical activity, assessing 1130 a cognitive disorder based on the excessive bioelectrical activity, and 1140 controlling therapy to treat the cognitive disorder for targets other than the hippocampus. Besides the hippocampus, targets for sensing excessive bioelectrical activity and delivering electrical stimulation delivery in the manner of FIG. 11 can include the hippocampal region (e.g., dentate gyms, hippocampus proper and subicular complex). Further targets can include the entorhinal, perirhinal, and parahippocampal cortices, among the other brain targets referenced herein.

It is noted that this disclosure is presented in an exemplary format and not in a limiting manner. The scope of this disclosure is not limited to the specific embodiments presented herein. The various options shown herein can be selectively employed and modified by one having ordinary skill in the art to practice the subject matter of this disclosure.

We claim:

1. A method for treating a cognitive disorder of a patient, comprising:
    sensing one or more bioelectrical brain signals of the patient using one or more electrodes;
    detecting non-motor epileptiform bioelectrical activity from the one or more bioelectrical brain signals, wherein the non-motor epileptiform bioelectrical activity is not temporally associated with a physical event indicative of a seizure;
    assessing a degenerative cognitive disorder of the patient based on the non-motor epileptiform bioelectrical activity; and
    controlling delivery of an electrical stimulation therapy to the brain of the patient to treat the degenerative cognitive disorder, the delivery of the electrical stimulation therapy controlled based on the assessment of the degenerative cognitive disorder, wherein detecting, assessing, and controlling delivery are each performed at least in part by control circuitry.

2. The method of claim 1, further comprising tracking a second indicator of the cognitive disorder, wherein the second indicator is not based on a sensed bioelectrical signal and the assessment of the cognitive disorder is further based on the second indicator.

3. The method of claim 2, wherein the assessment of the cognitive disorder is based on corroboration between the second indicator and the non-motor epileptiform bioelectrical activity.

4. The method of claim 2, wherein the second indicator is measured based on the patient's performance on a cognitive test testing cognitive ability.

5. The method of claim 2, wherein the second indicator comprises an input by a user to an external programmer.

6. The method of claim 1, further comprising, for at least one episode of non-motor epileptiform bioelectrical activity, confirming that the episode is not temporally associated with a physical event indicative of a motor seizure.

7. The method of claim 6, further comprising receiving a signal from a sensor, the sensor monitoring for a physical non-bioelectrical manifestation of the motor seizure, wherein the signal is used to confirm that the episode is not temporally associated with the physical event.

8. The method of claim 1, wherein assessing the cognitive disorder comprises determining whether episodes of the non-motor epileptiform bioelectrical activity are changing in one or more of intensity, duration, and frequency of occurrence.

9. The method of claim 1, wherein each episode of non-motor epileptiform bioelectrical activity is detected as one or more of an irregular spike, a sharp wave, and a spike-and-wave complex that stands out as a transient in the sensed bioelectrical brain signal.

10. The method of claim 1, wherein detecting non-motor epileptiform bioelectrical activity comprises detecting excessive hippocampal bioelectrical activity from the one or more bioelectrical brain signals.

11. The method of claim 1, wherein the epileptiform bioelectrical activity is associated with a state of the patient wherein symptoms are not yet identifiable.

12. The method of claim 1, wherein the electrical stimulation therapy decreases one or more of the intensity, duration, and frequency of occurrence of episodes of the non-motor epileptiform bioelectrical activity associated with the cognitive disorder.

13. The method of claim 1, wherein controlling the delivery of the electrical stimulation therapy based on the assessment comprises increasing intensity of the electrical stimulation therapy if the cognitive disorder is assessed to be worsening.

14. The method of claim 1, wherein controlling the delivery of the electrical stimulation therapy based on the assessment comprises:
    increasing the intensity of the electrical stimulation therapy based on episodes of the non-motor epileptiform bioelectrical activity increasing in one or more of intensity, duration, and frequency of occurrence; and
    decreasing the intensity of the electrical stimulation therapy based on episodes of the non-motor epileptiform bioelectrical activity decreasing in one or more of intensity, duration, and frequency of occurrence.

15. The method of claim 1, wherein controlling the delivery of the electrical stimulation therapy comprises initiating the delivery of a series of pulses in response to the detection of each episode of non-motor epileptiform bioelectrical activity.

16. The method of claim 1, wherein the control circuitry is contained within an implantable medical device.

17. A system for treating a degenerative cognitive disorder of a patient comprising:
    a plurality of electrodes on one or more leads;
    sensing circuitry configured to sense one or more bioelectrical brain signals of the patient using at least one electrode of the plurality of electrodes;
    a stimulation generator configured to deliver an electrical stimulation therapy to the brain to treat the degenerative cognitive disorder of the patient, the electrical stimulation therapy delivered through one or more electrodes of the plurality of electrodes; and
    control circuitry configured to detect non-motor epileptiform bioelectrical activity from the one or more bioelectrical brain signals, assess a degenerative cognitive disorder of the patient based on the non-motor epileptiform bioelectrical activity, and control delivery of the electrical stimulation therapy to the brain based on the assessment of the degenerative cognitive disorder, wherein the non-motor epileptiform bioelectrical activity is not associated with a physical manifestation of a seizure.

18. The system of claim 17, wherein the control circuitry is configured to track a second indicator of the cognitive disorder, wherein the second indicator is not based on a sensed bioelectrical signal and the assessment of the cognitive disorder by the control circuitry is based on the second indicator.

19. The system of claim 18, wherein the control circuitry is configured to assess the cognitive disorder based on corroboration between the second indicator and the non-motor epileptiform bioelectrical activity.

20. The system of claim 18, further comprising an external device, wherein the external device is configured to administer a cognitive test to the patient, and the second indicator is measured based on the patient's performance on the cognitive test.

21. The system of claim 17, further comprising a sensor configured to output a signal indicative of a physical non-bioelectrical manifestation of a motor seizure, wherein the control circuitry is configured to, for at least one episode of non-motor epileptiform bioelectrical activity, confirm that the episode is not temporally associated with a physical event indicative of the motor seizure based on the signal.

22. The system of claim 17, wherein the control circuitry is configured to assess the cognitive disorder by determining whether the non-motor epileptiform bioelectrical activity is changing in one or more of intensity, duration, and frequency of occurrence.

23. The system of claim 17, wherein the control circuitry is configured to detect each episode of the non-motor epileptiform bioelectrical activity as an irregular spike, a sharp wave, and a spike-and-wave complex that stands out as a transient in the sensed bioelectrical brain signal.

24. The system of claim 17, wherein the control circuitry comprises control circuitry configured to detect excessive hippocampal bioelectrical activity from the one or more bioelectrical brain signals, assess a degenerative cognitive disorder of the patient based on the excessive hippocampal bioelectrical activity, and control delivery of the electrical stimulation therapy to the brain based on the assessment of the cognitive disorder.

25. The system of claim 17, wherein the non-motor epileptiform bioelectrical activity is not temporally associated with a physical event indicative of a seizure.

26. The system of claim 17, wherein the electrical stimulation therapy decreases one or more of the intensity, duration, and frequency of occurrence of episodes of the non-motor epileptiform bioelectrical activity associated with the cognitive disorder.

27. The system of claim 17, wherein the control circuitry is configured to control the delivery of the electrical stimulation therapy based on the assessment of the non-motor epileptiform bioelectrical activity by increasing intensity of the electrical stimulation therapy if the cognitive disorder is assessed to be worsening.

28. The system of claim 17, wherein the control circuitry is configured to control the delivery of the electrical stimulation therapy based on the assessment of the non-motor epileptiform bioelectrical activity by:
    increasing the intensity of the electrical stimulation therapy based on episodes of the non-motor epileptiform bioelectrical activity increasing in one or more of intensity, duration, and frequency of occurrence; and
    decreasing the intensity of the electrical stimulation therapy based on episodes of the non-motor epileptiform bioelectrical activity decreasing in one or more of intensity, duration, and frequency of occurrence.

29. The system of claim 17, wherein the control circuitry is configured to control the delivery of the electrical stimulation therapy by initiating the delivery of a series of pulses in response to the detection of each episode of non-motor epileptiform bioelectrical activity.

30. The system of claim 17, wherein the control circuitry is fully contained within a housing of an implantable medical device.

31. The system of claim 17, wherein the control circuitry is contained, at least in part, within an external device.

32. A system for treating a cognitive disorder of a patient, comprising:
- means for sensing one or more bioelectrical brain signals of the patient;
- means for detecting non-motor epileptiform bioelectrical activity from the one or more bioelectrical brain signals, wherein the non-motor epileptiform bioelectrical activity is not associated with an outward physical event;
- means for assessing a degenerative cognitive disorder of the patient based on the non-motor epileptiform bioelectrical activity; and
- means for delivering an electrical stimulation therapy to the brain of the patient to treat the degenerative cognitive disorder, the delivery of the electrical stimulation therapy controlled based on the assessment of the degenerative cognitive disorder.

33. The system of claim 32, wherein the non-motor epileptiform bioelectrical activity is not temporally associated a physical event indicative of a seizure.

34. A non-transitory computer-readable medium comprising instructions executable by a processor to cause circuitry to:
- sense one or more bioelectrical brain signals from the brain of a patient;
- detect non-motor epileptiform bioelectrical activity from the one or more bioelectrical brain signals, wherein the non-motor epileptiform bioelectrical activity is not associated with a physical event indicative of a seizure;
- assess a degenerative cognitive disorder of the patient based on the non-motor epileptiform bioelectrical activity; and
- control delivery of an electrical stimulation therapy to the brain of the patient to treat the degenerative cognitive disorder, the delivery of the electrical stimulation therapy controlled based on the assessment of the degenerative cognitive disorder.

35. The non-transitory computer-readable medium of claim 34, wherein the instructions are executable by a processor to cause circuitry to detect the non-motor epileptiform bioelectrical activity from the one or more bioelectrical brain signals, wherein the non-motor epileptiform bioelectrical activity is not temporally associated with a physical event indicative of a seizure.

36. A method for treating a cognitive disorder of a patient, comprising:
- sensing one or more bioelectrical brain signals of the patient using one or more electrodes;
- detecting excessive hippocampal bioelectrical activity from the one or more bioelectrical brain signals, wherein the excessive hippocampal bioelectrical activity comprises epileptiform bioelectrical activity unassociated with an outward physical manifestation;
- assessing a degenerative cognitive disorder of the patient based on the epileptiform bioelectrical activity; and
- controlling delivery of an electrical stimulation therapy to the brain of the patient to treat the cognitive disorder, the delivery of the electrical stimulation therapy controlled based on the assessment of the cognitive disorder, wherein detecting, assessing, and delivering are each performed at least in part by control circuitry.

37. The method of claim 36, wherein the epileptiform bioelectrical activity is indicative of one or more epileptiform bioelectrical activity episodes, and wherein assessing a degenerative cognitive disorder of the patient based on the epileptiform bioelectrical activity comprises assessing the degenerative cognitive disorder of the patient based on the one or more epileptiform bioelectrical activity episodes.

38. The method of claim 36, wherein the epileptiform bioelectrical activity is not temporally associated with a physical event indicative of a seizure.

39. The method of claim 36, wherein the epileptiform bioelectrical activity is associated with a state of the patient wherein symptoms are not yet identifiable.

* * * * *

UNITED STATES PATENT AND TRADEMARK OFFICE
CERTIFICATE OF CORRECTION

| | |
|---|---|
| PATENT NO. | : 8,918,176 B2 |
| APPLICATION NO. | : 13/777091 |
| DATED | : December 23, 2014 |
| INVENTOR(S) | : Nelson et al. |

It is certified that error appears in the above-identified patent and that said Letters Patent is hereby corrected as shown below:

In the Claims

Col. 41, Line 20: "not temporally associated a" should read --not temporally associated with a--

Signed and Sealed this
Ninth Day of June, 2015

Michelle K. Lee
*Director of the United States Patent and Trademark Office*